United States Patent
Klapproth et al.

(10) Patent No.: US 11,046,820 B2
(45) Date of Patent: Jun. 29, 2021

(54) THREE-DIMENSIONAL POLYMER NETWORKS AND THEIR USE

(71) Applicant: Safeguard Biosystems Holdings Ltd., London (GB)

(72) Inventors: Holger Klapproth, Freiburg (DE); Sonja Bednar, Gundelfingen (DE)

(73) Assignee: Safeguard Biosystems Holdings Ltd., London (GB)

( * ) Notice: Subject to any disclaimer, the term of this patent is extended or adjusted under 35 U.S.C. 154(b) by 0 days.

(21) Appl. No.: 16/351,218

(22) Filed: Mar. 12, 2019

(65) Prior Publication Data
US 2019/0211159 A1 Jul. 11, 2019

Related U.S. Application Data

(63) Continuation of application No. 16/011,790, filed on Jun. 19, 2018, now Pat. No. 10,273,336.

(30) Foreign Application Priority Data

Jun. 19, 2017 (EP) .................................... 17176572

(51) Int. Cl.
| | |
|---|---|
| C08J 3/075 | (2006.01) |
| C08K 3/32 | (2006.01) |
| C08K 5/07 | (2006.01) |
| C08L 33/26 | (2006.01) |
| C08F 12/30 | (2006.01) |
| C08L 25/18 | (2006.01) |
| B01L 3/00 | (2006.01) |
| G01N 33/543 | (2006.01) |

(52) U.S. Cl.
CPC ............. *C08J 3/075* (2013.01); *B01L 3/00* (2013.01); *C08F 12/30* (2013.01); *C08K 3/32* (2013.01); *C08K 5/07* (2013.01); *C08L 25/18* (2013.01); *C08L 33/26* (2013.01); *G01N 33/54366* (2013.01); *C08F 2810/20* (2013.01); *C08K 2003/324* (2013.01); *C08L 2312/00* (2013.01)

(58) Field of Classification Search
CPC ... C08J 3/075; C08K 3/32; C08K 5/07; C08K 2003/324; C08L 33/26; C08L 25/18; C08L 2312/00; C08F 12/30; C08F 2810/20
USPC ......................................................... 524/547
See application file for complete search history.

(56) References Cited

U.S. PATENT DOCUMENTS

| | | | | |
|---|---|---|---|---|
| 9,738,926 B2* | 8/2017 | Klapproth | .............. | C12N 11/08 |
| 9,914,961 B2* | 3/2018 | Klapproth | .............. | C12N 11/08 |
| 10,273,336 B2* | 4/2019 | Klapproth | .............. | C08F 12/30 |
| 2004/0053298 A1* | 3/2004 | Mirzabekov | ........... | C07K 17/08 |
| | | | | 435/6.1 |
| 2005/0042363 A1 | 2/2005 | Kukhtin et al. | | |
| 2008/0293592 A1* | 11/2008 | Ruhe | ...................... | C12N 11/08 |
| | | | | 506/15 |
| 2009/0042741 A1* | 2/2009 | Northen | ........... | G01N 33/54386 |
| | | | | 506/20 |
| 2018/0362719 A1 | 12/2018 | Klapproth et al. | | |

FOREIGN PATENT DOCUMENTS

| | | |
|---|---|---|
| EP | 3181700 A1 | 6/2017 |
| WO | 2005/108992 A1 | 11/2005 |
| WO | 2017/103128 A1 | 6/2017 |

OTHER PUBLICATIONS

Rendl etal. "Simple One-step Process for Immobilization of Biomolecules on Polymer Substrates Based on Surface-Attached Polymer Networks", ACS Publications, Langmuir (2011), vol. 27, pp. 6116-6123. (Year: 2011).*
Horaketal. "Superporous poly(2-hydroxyethyl methacrylate) based scaffolds: Preparation and characterization", Polymer, vol. 49 (2008), pp. 2046-2054. (Year: 2008).*
Extended European Search Report and Opinion dated Mar. 15, 2016 in EP 15201355.3.
Extended European Search Report and Opinion dated Oct. 12, 2017 in EP 17176572.0.
International Search Report dated Apr. 12, 2017 in PCT/EP2016/081457.
Written Opinion of the International Search Authority dated Apr. 12, 2017 in PCT/EP2016/081457.
International Search Report and Written Opinion of the International Searching Authority dated Jul. 5, 2018 in PCT/EP2018/066148.
Ahmed, 2015, "Hydrogel: Preparation, characterization, and applications: A review," Journal of Advanced Research 6:105-121.
Arrua et al., 2009, "Macroporous Monolithic Polymers: Preparation and Applications," Materials 2:2429-2466.
Baader et al., 2011, "Polysaccharide microarrays with a CMOS based signal detection unit," Biosensors and Bioelectronics 26(5):1839-1846.
Glotov et al., 2015, "Detection of human genome mutations associated with pregnancy complications using 3-D microarray based on macroporous polymer monoliths," Talanta 147:537-546 (abstract only).
Horak et al., 2008, "Superporous poly(2-hydroxyethyl methacrylate) based scaffolds: Preparation and characterization," Polymer 49:2046-2054.

(Continued)

*Primary Examiner* — Michael Bernshteyn

(74) *Attorney, Agent, or Firm* — Biospark Intellectual Property Law

(57) ABSTRACT

The disclosure provides three-dimensional cross-linked polymer networks transport channels, arrays comprising the networks, processes for making the networks, and uses of the networks and arrays.

23 Claims, 10 Drawing Sheets

(56) References Cited

OTHER PUBLICATIONS

Jerabek et al., 1992, "Accessibility of the Gel Phase in Macroporous Network Polymers: A Comparison of the Fluorescence Probe and Inverse Steric Exclusion Chromatography Techniques," Journal of Polymer Science: Part A: Polymer Chemistry 30:605-611.
Nakayama et al., 1995, "Design and Properties of Photocurable Electroconductive Polymers for Use in Biosensors," ASAIO Journal 41:M418-M421.
Murphy et al., 1992, "Synthetic Hydrogels: Part 9—Preparation and Characterisation of Macroporous Hydrophilic Matrices," J. Mater. Chem. 2(10):1007-1013.
Okay, 2000, "Macroporous copolymer networks," Prog. Polym. Sci. 25:711-779.
Oxley et al., 1993, "Macroporous hydrogels for biomedical applications: methodology and morphology," Biomaterials 14(14):1064-1072.
Rendl et al., 2011, "Simple One-Step Process for Immobilization of Biomolecules on Polymer Substrates Based on Surface-Attached Polymer Networks," Langmuir 27:6116-6123.
Tanaka, 1980, "Gels," Scientific American, 244(1): 124-138.

\* cited by examiner

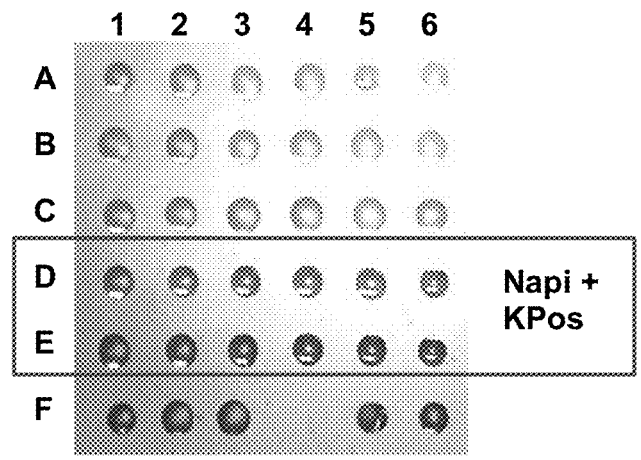
Fig. 11A
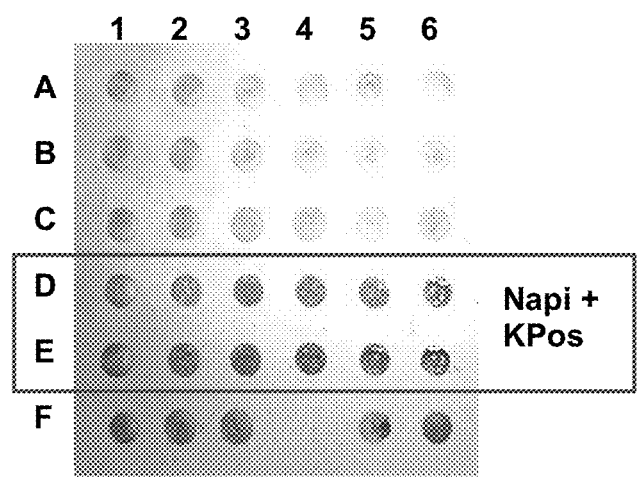
Fig. 11B
| Spot No | Name | Final Napi | Final KPos. |
|---|---|---|---|
| D1, E1 | NaPi + Kpos 1 | 350 mM | 50 mM |
| D2, E2 | NaPi + Kpos 2 | 350 mM | 100 mM |
| D3, E3 | NaPi + Kpos 3 | 350 mM | 150 mM |
| D4, E4 | NaPi + Kpos 4 | 350 mM | 200 mM |
| D5, E5 | NaPi + Kpos 5 | 350 mM | 250 mM |
| D6, E6 | NaPi + Kpos 6 | 350 mM | 300 mM |
Fig. 11C

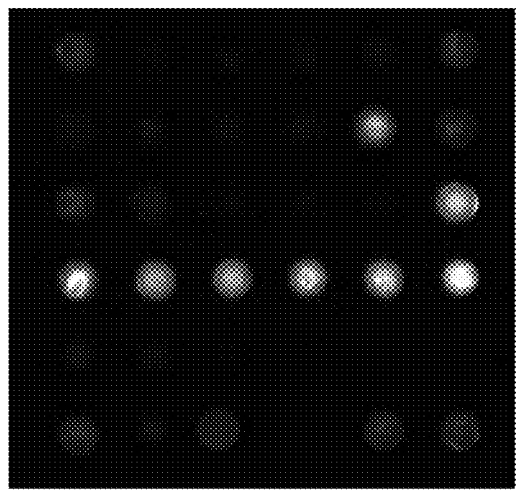
Fig. 12A
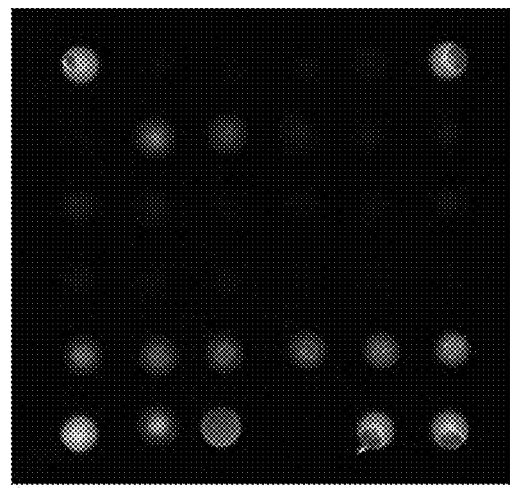
Fig. 12B
|   | 1 | 2 | 3 | 4 | 5 | 6 |
|---|---|---|---|---|---|---|
| A | LL | | | | | LL |
| B | | Salmonella | Salmonella | | All staph | |
| C | | | | | | S. aureus |
| D | S. aureus | S. aureus | S. aureus | S. aureus | S. aureus | S. aureus |
| E | E. coli | E. coli | E. coli | E. coli | E. coli | E. coli |
| F | LL | E. coli | PCR control | | LL | LL |
Fig. 12C

THREE-DIMENSIONAL POLYMER NETWORKS AND THEIR USE

1. CROSS-REFERENCE TO RELATED APPLICATIONS

This application is a continuation of U.S. application Ser. No. 16/011,790, filed Jun. 19, 2018, which claims priority under 35 U.S.C. § 119 to European application no. 17176572.0, filed Jun. 19, 2017, the contents of which are incorporated herein in their entireties by reference thereto.

2. BACKGROUND

U.S. Publication No. 2008/0293592 describes a method for covalently immobilizing probe-biomolecules on organic surfaces by means of photoreactive cross-linking agents. The method has in practice proven to be advantageous particularly because it permits an immobilization of probe biomolecules on unreactive surfaces, such as silanized glass supports and substrates made of standard commercial plastics. A polymer is used in the method described in US 2008/0293592 to form a type of three-dimensional network onto which the probe biomolecules can be bonded, either at the network's surface or in the inside of the network. Compared to an organic surface on which the probe biomolecules are only immobilized in two-dimensional form, the three-dimensional immobilization of the biomolecules in the polymer and/or copolymer network permits a higher density of the probe biomolecules on the organic surface. This increases the amount of analyte which can be bonded per surface unit of the organic surface. Use of the surface as biological sensor thus gives rise to a higher measurement accuracy and a high measurement dynamic.

However, a disadvantage of the methods and polymer networks described in U.S. 2008/0293592 is that analyte molecules or analyte components which bind to probe biomolecules arranged on or close to the surface of the polymer network can block the network. Further analyte molecules or analyte constituents can then no longer bind as well to as yet unbound probe biomolecules which are arranged at a greater distance from the surface of the network in its interior.

Thus, there is a need for improved polymer networks.

3. SUMMARY

This disclosure provides three-dimensional polymer networks comprising cross-linked polymer chains, e.g., water-soluble polymer chains, and one or more transport channels. The transport channels permit molecules in solution, e.g., analyte molecules, to access the polymer chains within the network. In certain aspects, the polymer chains are cross-linked to probe molecules, and the transport channels provide a greater surface area for binding of analytes to probe molecules.

The networks are suitably covalently attached to a surface. As implied in the preceding paragraph, one or more probes, such as a biomolecule, can be immobilized on the surface of the network and throughout the interior of the network, providing a sensor for detecting the presence of and/or measuring the amount of an analyte in a sample. For example, nucleic acid probes can be used to detect complementary nucleic acids present in a sample and antibody probes can be used to detect antigens present in a sample. The networks of the disclosure allow for faster hybridization of a given amount of analyte than networks lacking transport channels because the transport channels can effectively increase the surface area of the network, exposing more probes to the sample in a given amount of time. Additionally, the networks of the disclosure can bind more analyte than the same volume of a transport channel-free network because the transport channels decrease or eliminate the problem whereby analyte or other components of a sample bound to probes at or near the surface of the network block access to probes located in the interior of the network. Another advantage of the networks of the disclosure is that the high amount of analyte loading made possible by the transport channels allows for a more sensitive detection of analyte than may be possible with a transport channel-free network, i.e., the signal to noise ratio can be improved compared to transport channel-free networks because a given amount of analyte can be concentrated in a smaller network volume. Yet another advantage of the networks of the disclosure is that the high analyte loading made possible by the transport channels allows for quantification of a wider range of analyte concentrations compared to transport channel-free networks.

This disclosure also provides arrays comprising a plurality of the three-dimensional networks of the disclosure and a substrate. Arrays of the disclosure can be used to detect and/or measure one or more analytes in one or more samples simultaneously. The arrays of the disclosure can be washed and reused, providing a significant cost advantage over single use arrays. Another advantage of the arrays of the disclosure is that they can be manufactured in a simple manner because all of the components needed to make an individual network can be applied as a single mixture onto a surface of the substrate during the manufacturing process.

This disclosure also provides processes for making the three-dimensional networks and arrays of the disclosure. The three-dimensional networks of the disclosure can be made by cross-linking a polymer in the presence of at least two types of salt crystals, preferably needle-shaped salt crystals and compact salt crystals, and subsequently dissolving the salt crystals to leave behind transport channels in the cross-linked polymer network. Without being bound by theory, the inventors believe that the presence of compact salt crystals during cross-linking results in a sponge-like polymer with short channels that are penetrated by long channels created by the presence of the needle-shaped salt crystals during cross-linking.

This disclosure also provides processes for using the three-dimensional networks and arrays of the disclosure to detect and/or measure an analyte in a sample, preferably a liquid sample.

4. BRIEF DESCRIPTION OF THE FIGURES

FIG. 1 shows a diagrammatic representation of a mixture which has a probe biomolecule (1) and a polymer (3) comprising two photoreactive groups (4) per molecule dissolved in an aqueous salt solution (as described in Section 5.3.1).

FIG. 2 shows shows a cross-section through a drop of a mixture (5), such as that shown in FIG. 1, having a surface (10) located at a spot (7) of a surface (2) which can be situated on a holder (6). The surface is preferably that of an organic substrate or a substrate with an organic containing. The substrate is preferably rigid. The holder can be a heated holder or a chilled holder to permit controlled crystallization of the salts in the aqueous salt solution.

FIGS. 11A-11C show a biochip with 6 rows (A-F) and 6 columns (1-6) of polymer networks prior to (FIG. 11A) and after (FIG. 11B) drying, with shows the salt concentrations used to make the polymer networks of rows D and E show in FIG. 11C. The polymer networks of rows D and E were made using an aqueous salt solution containing both sodium phosphate and potassium phosphate. The remaining rows were made using an aqueous salt solution containing only sodium phosphate, at a concentration of 350 mM. The polymer networks of rows D and E look more round and homogeneous.

FIGS. 12A-12C show the results of hybridization of a PCR reaction product using S. aureus and E. coli-specific primer pairs to arrays according to FIG. 12A-FIG. 12C. FIG. 12A shows hybridization to an array of PCR product amplified from 100 copies of S. aureus DNA. FIG. 12B shows hybridization to an array of PCR product amplified from 100 copies of E. coli DNA. FIG. 12C shows the probe map for the arrays shown in FIG. 12A and FIG. 12B. E. coli=E. coli probe; Salmonella=Salmonella probe (to which the E. coli PCR product shows some cross-reactivity); Allstaph=a pan Staphylococcus probe; S. aureus=S. aureus probe; PCR control=probe to detect internal control for PCR amplification process; LL=landing lights, which are fluorophore-labeled oligonucleotides cross-linked to the polymer chains in the networks used as array controls.

Figure 13:
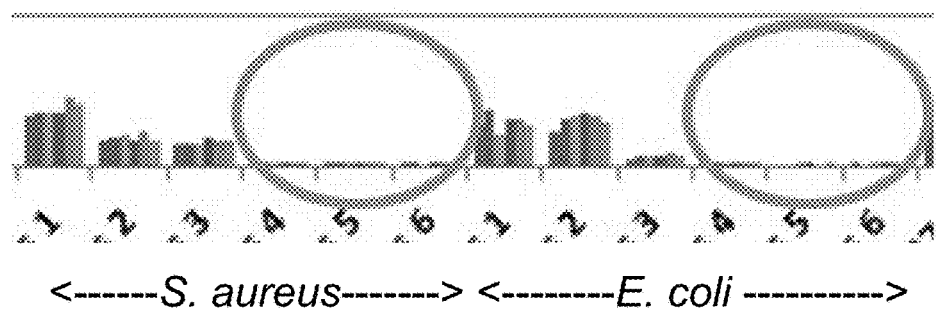

FIG. 13 shows quantification of fluorescence signals from hybridization of PCR product amplified using S. aureus or E. coli-specific primer pairs in the absence of template, representing background "noise". No. 1 represents spot D1, E1; no. 2 represents the spot D1, E2; no. 3 represents spot D1, E3; no. 4 represents the spot D1, E4; no. 5 represents spot D1, E5; and no. 6 represents the spot D1, E6.

5. DETAILED DESCRIPTION

5.1. Three-Dimensional Polymer Networks

The three-dimensional networks of the disclosure comprise a cross-linked polymer, e.g., a polymer according to Rendl et al., 2011, Langmuir 27:6116-6123 or US 2008/0293592, the contents of which are incorporated by reference in their entireties herein. The three-dimensional networks of the disclosure further comprise one or more transport channels and can optionally further comprise one or more probes immobilized on the network, e.g., by cross-linking to the polymer chains.

The networks of the disclosure can have a mesh size (measured in the hydrated state of the network) of, for example, 5 to 75 nm (e.g., 10 to 20 nm, 10 to 30 nm, 10 to 40 nm, 10 to 50 nm, 20 to 30 nm, 20 to 40 nm, 20 to 50 nm, 30 to 40 nm, 30 to 50 nm, or 40 to 50 nm). The "hydrated state of the network" means that the network is at equilibrium with respect to water absorption, i.e., it absorbs in aqueous solution as much water as it emits.

Polymers that can be used to make the networks are described in Section 5.1.1. Cross-linkers than can be used to make the networks are described in Section 5.1.2. Features of the one or more transport channels are described in Section 5.1.3. Probes that can be immobilized on the networks are described in Section 5.1.4.

5.1.1. Polymers

The three-dimensional networks of the disclosure can comprise a cross-linked homopolymer, copolymer, mixtures of homopolymers, mixtures of copolymers, or mixtures of one or more homopolymers and one or more copolymers. The term "polymer" as used herein includes both homopolymers and/or copolymers. The term "copolymer" as used herein includes polymers polymerized from two or more types of monomers (e.g., bipolymers, terpolymers, quaterpolymers, etc.). Copolymers include alternating copolymers, periodic copolymers, statistical copolymers, random copolymers, block copolymers, linear copolymers and branched copolymers. The three-dimensional networks of the disclosure can comprise any combination of the foregoing types of polymers. Reagents and methods for making such polymers are known in the art (see, e.g., Ravve, A., *Principles of Polymer Chemistry*, Springer Science+Business Media, 1995; Cowie, J. M. G., *Polymers: Chemistry & Physics of Modern Materials*, 2$^{nd}$ Edition, Chapman & Hall, 1991; Chanda, M., *Introduction to Polymer Science and Chemistry: A Problem-Solving Approach*, 2$^{nd}$ Edition, CRC Press, 2013; Nicholson, J. W., *The Chemistry of Polymers*, 4$^{th}$ Edition, RSC Publishing, 2012; the contents of each of which are herein incorporated by reference in their entirety).

Preferred polymers are hydrophilic and/or contain hydrophilic groups. The polymer is preferably water-soluble. In an embodiment, the polymer is a copolymer that has been polymerized from two or more species of monomers selected to provide a desired level of water solubility. For example, water solubility of a copolymer can be controlled by varying the amount of a charged monomer, e.g., sodium 4-vinylsulfonate, used to make the copolymer.

When cross-linked, water-soluble polymers form water-swellable gels or hydrogels. Hydrogels absorb aqueous solutions through hydrogen bonding with water molecules. The total absorbency and swelling capacity of a hydrogel can be controlled by the type and degree of cross-linkers used to make the gel. Low cross-link density polymers generally have a higher absorbent capacity and swell to a larger degree than high cross-link density polymers, but the gel strength of high cross-link density polymers is firmer and can maintain network shape even under modest pressure.

A hydrogel's ability to absorb water is a factor of the ionic concentration of the aqueous solution. In certain embodiments, a hydrogel of the disclosure can absorb up to 50 times its weight (from 5 to 50 times its own volume) in deionized, distilled water and up to 30 times its weight (from 4 to 30 times its own volume) in saline. The reduced absorbency in saline is due to the presence of valence cations, which impede the polymer's ability to bond with the water molecule.

The three-dimensional network of the disclosure can comprise a copolymer that has been polymerized from one, two, thee, or more than three species of monomers, wherein one, two, three or more than three of the species of monomers have a polymerizable group independently selected from an acrylate group (e.g., acrylate, methacrylate, methyl methacrylate, hydroxyethyl methacrylate, ethyl acrylate, 2-phenyl acrylate), an acrylamide group (e.g., acrylamide, methacrylamide, dimethylacrylamide, ethylacrylamide), an itaconate group (e.g., itaconate, 4-methylitaconate, dimethyl itaconate) and a styrene group (e.g. styrene, 4-methyl styrene, 4-ethoxystyrene). Preferred polymerizable groups are acrylate, methacrylate, ethacrylate, 2-phenyl acrylate, acrylamide, methacrylamide, itaconate, and styrene. In some embodiments, one of the monomers used to make the copolymer is charged, e.g., sodium 4-vinylbenzenesulfonate.

Figure 7:
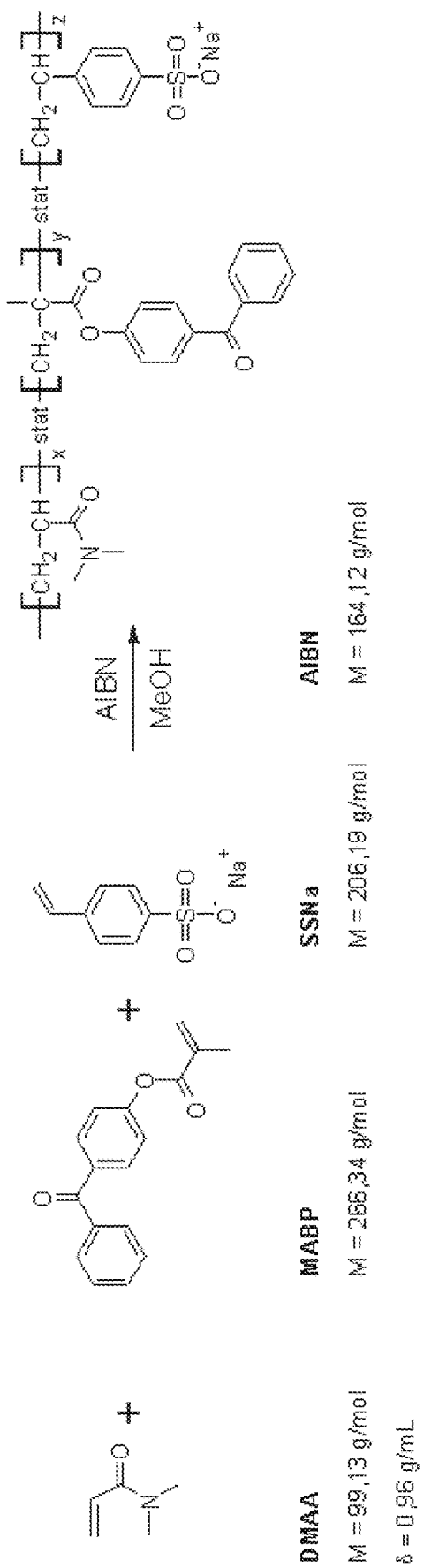
FIG. 7 shows a reaction pathway for the formation of p(Dimethyacryamide co Methacryloyl-Benzophenone co Sodium 4-vinylbenzenesulfonate).

The polymer used to make a network of the disclosure can comprise at least one, at least two, or more than two cross-linker groups per molecule. A cross-linker group is a group that covalently bonds the polymer molecules of the network to each other and, optionally, to probes and/or a substrate. Copolymers that have been polymerized from two or more monomers (e.g., monomers having a polymerizable group independently selected from those described in the preceding paragraph), at least one of which comprises a cross-linker, are suitable for making a three-dimensional network of the disclosure. Exemplary cross-linkers are described in Section 5.1.2. A preferred monomer comprising a cross-linker is methacryloyloxybenzophenone (MABP) (see FIG. 7).

In a preferred embodiment, the copolymer is a bipolymer or a terpolymer comprising a cross-linker. In a particularly preferred embodiment, the copolymer comprises p(Dimethyacryamide co Methacryloyl-Benzophenone co Sodium 4-vinylbenzenesulfonate) (see FIG. 7).

5.1.2. Cross-Linkers

Cross-linking reagents (or cross-linkers) suitable for making the cross-links in the three-dimensional networks include those activated by ultraviolet light (e.g., long wave UV light), visible light, and heat. Exemplary cross-linkers activated by UV light include benzophenone, thioxanthones (e.g., thioxanthen-9-one, 10-methylphenothiazine) and benzoin ethers (e.g., benzoin methyl ether, benzoin ethyl ether). Exemplary cross-linkers activated by visible light include ethyl eosin, eosin Y, rose bengal, camphorquinone and erythirosin. Exemplary cross-linkers activated by heat include 4,4' azobis(4-cyanopentanoic) acid, and 2,2-azobis [2-(2-imidazolin-2-yl) propane] dihydrochloride, and benzoyl peroxide. Other cross-linkers known in the art, e.g., those which are capable of forming radicals or other reactive groups upon being irradiated, may also be used.

5.1.3. Transport Channels

The three-dimensional networks of the disclosure contain one or more transport channels.

Transport channels can allow access to the interior of the network. Although transport channels can have a relatively large cross-section, the network can remain mechanically stable because the mesh size of the network can be significantly smaller than the transport channel cross-section.

The transport channels can form a sort of highway, through which analytes can enter quickly in and out of the interior of the network. The transport of the analytes can be effected in the transport channels by diffusion and/or convection.

Transport channels are formed when a network is formed by cross-linking polymer chains in the presence of salt crystals, as described in Section 5.3. After salt crystals are washed away, transport channels are left behind.

Without being bound by theory, the inventors believe that the methods of making the networks in the disclosure result the formation of at least two types of salt crystals resulting from different metal ion—salt ion pairings. When the salt crystals are washed away, at least two types of transport channels are left behind, according to the principle of the "lost" form. The transport channels allow analytes to penetrate into the interior of the network and specifically bind a probe located in the interior of the network. Additionally, the transport channels allow unbound analytes to exit the interior of the network after washing, reducing the amount of nonspecific signal from analytes "stuck" within the network.

One type of transport channel is believed to be a long channel created from needle-shaped salt crystals. As used herein, a "long channel" is an elongated passage in a network that (1) is substantially straight, and (2) in the hydrated state of the network, has a minimum cross-section that is at least 300 nm and a length that is at least three times, preferably five times, and more preferably at least ten times, the minimum cross-section of the passage. For example, the length of the long channel can be 3 to 15 times, 5 to 10 times, or 10 to 15 times the minimum cross-section of the long channel. A long channel that is "substantially straight" is one which extends from a point of nucleation in one direction without changing direction more than 45 degrees in any direction, i.e., the X, Y or Z direction. Because long channels arise from needle-shaped crystals that form from a common nucleation point, the networks of the disclosure might include groups of (e.g., 5, 10 or more) long channels that converge at a point located within the network corresponding to the original nucleation point of crystallization. Long channels are typically arranged such that, starting from the surface of the network towards the interior, the lateral distance between the long channels decreases.

In other aspects, one type of transport channel is believed to be a short channel, for example formed from cubic or rod-shaped crystals. As used herein, a "short channel" is a passage in a network that (1) is substantially straight, and (2) in the hydrated state of the network, has a minimum cross-section that is preferably at least 10 times the mesh size of the network and a length that is less than three times (e.g., can range from 1 time to 2.75 times, from 1 time to 2.5 times, from 1 time to 2 times, or from 1 time to 1.5 times) the minimum cross-section of the passage. A short channel that is "substantially straight" is one which extends from a point of nucleation in one direction without changing direction more than 45 degrees in any direction, i.e., the X, Y or Z direction. To maintain network strength, a short channel preferably has a cross-section of no greater than $1/20^{th}$ of the network width or diameter, for example for a network that is in the form of a "spot" on an array with a diameter of 200 µm, the cross-section of the short channel is preferably no greater than 10 µm, and for a spot on an array with a diameter of 100 µm, the cross-section of the short channel is preferably no greater than 5 µm. In certain aspects, the cross-section of the short channel is about 20 nm or greater, about 50 nm or greater, about 100 nm or greater, about 250 nm or greater, at least 500 nm or greater, or about 1 µm or greater. The short channels in a network can have approximately (e.g., +/−10% or +/−25%) the same diameter or different diameters. In particular embodiments, the short channels in a network have a diameter ranging between any two of the foregoing dimensions, e.g., they can range from 100 nm to 10 µm, from 50 nm to 1 µm, from 500 nm to 5 µm, from 250 nm to 10 µm, and so on and so forth.

Without being bound by theory, the inventors believe that the short channels create a sponge polymer that is penetrated by the long channels.

5.1.4. Probes

A probe immobilized on the network of the disclosure can be a biomolecule or a molecule that binds a biomolecule, e.g., a partner of a specifically interacting system of complementary binding partners (receptor/ligand). For example, probes can comprise nucleic acids and their derivatives (such as RNA, DNA, locked nucleic acids (LNA), and peptide nucleic acids (PNA)), proteins, peptides, polypeptides and their derivatives (such as glucosamine, antibodies, antibody fragments, and enzymes), lipids (e.g., phospholipids, fatty acids such as arachidonic acid, monoglycerides, diglycerides, and triglycerides), carbohydrates, enzyme inhibitors, enzyme substrates, antigens, and epitopes. Probes can also comprise larger and composite structures such as liposomes, membranes and membrane fragments, cells, cell lysates, cell fragments, spores, and microorganisms.

A specifically interacting system of complementary bonding partners can be based on, for example, the interaction of a nucleic acid with a complementary nucleic acid, the interaction of a PNA with a nucleic acid, or the enzyme/substrate, receptor/ligand, lectin/sugar, antibody/antigen, avidin/biotin or streptavidin/biotin interaction.

Nucleic acid probes can be a DNA or an RNA, for example, an oligonucleotide or an aptamer, an LNA, PNA, or a DNA comprising a methacyrl group at the 5' end (5' Acrydite™) Oligonucleotide probes can be, for example, 12 to 30, 14 to 30, 14 to 25, 14 to 20, 15 to 30, 15 to 25, 15 to 20, 16 to 30, 16 to 25, 16 to 20, 15 to 40, 15 to 45, 15 to 50, 15 to 60, 20 to 55, 18 to 60, 20 to 50, 30 to 90, 20 to 100, 20 to 60, 40 to 80, 40 to 100, 20 to 120, 20 to 40, 40 to 60, 60 to 80, 80 to 100, 100 to 120 or 12 to 150 nucleotides long. In preferred embodiments, the oligonucleotide probe is 15 to 60 nucleotides in length.

When using a nucleic acid probe, all or only a portion of the probe can be complementary to the target sequence. The portion of the probe complementary to the target sequence is preferably at least 12 nucleotides in length, and more preferably at least 15, at least 18 or at least 20 nucleotides in length. For nucleic acid probes of greater length than 40 or 50 nucleotides, the portion of the probe complementary to the target sequence can be at least 25, at least 30 or at least 35 nucleotides in length.

The antibody can be, for example, a polyclonal, monoclonal, or chimeric antibody or an antigen binding fragment thereof (i.e., "antigen-binding portion") or single chain thereof, fusion proteins comprising an antibody, and any other modified configuration of the immunoglobulin molecule that comprises an antigen recognition site, including, for example without limitation, single chain (scFv) and domain antibodies (e.g., human, camelid, or shark domain antibodies), maxibodies, minibodies, intrabodies, diabodies, triabodies, tetrabodies, vNAR and bis-scFv (see e.g., Hollinger and Hudson, 2005, Nature Biotech 23:1126-1136). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. "Antibody" also encompasses any of each of the foregoing antibody/immunoglobulin types.

Three-dimensional networks of the disclosure can comprise a single species of probe or more than one species of probe (e.g., 2, 3, 4, or 5 or more species). Three-dimensional networks can comprise more than one species of probe for the same target (e.g., antibodies binding different epitopes of the same target) and/or comprise probes that bind multiple targets.

The networks can comprise a labeled (e.g., fluorescently labeled) control probe molecule that can be used, for example, to measure the amount probe present in the network.

The probes can be distributed throughout the network (e.g., on a surface and the interior of a network). Preferably, at least one probe is spaced away from the surface of the network and adjoins at least one transport channel. A probe so located is then directly accessible for analyte molecules or analyte components through the transport channel. In some embodiments, a majority of the probes are located in the interior of the network.

The one or more probes can be immobilized on the network covalently or non-covalently. For example, a probe can be cross-linked to the cross-linked polymer or a probe can be non-covalently bound to the network (such as by binding to a molecule covalently bound to the network). In a preferred embodiment, one or more probes are cross-linked to the cross-linked polymer. In some embodiments, a majority of the probes are covalently bound in the interior of the network (e.g., such that at least a portion of the probes adjoin a transport channel).

Without being bound by theory, the inventors believe that the processes described in Section 5.3 for manufacturing three-dimensional networks in the presence of salt crystals (particularly phosphate salt crystals) may result in a greater concentration of probe molecule at or near the interface between the polymer and the transport channel due to electrostatic interactions between the probe molecules (particularly nucleic acid probe molecules) and the salt crystals. Accordingly, in some embodiments of the invention, the disclosure provides networks according to the disclosure in which the probe density is greater at the interface between the polymer and the transport channels than within regions of the polymer not abutting a transport channel. In various embodiments, the probe density it at least 10%, at least 20%, at least 30%, at least 40%, or at least 50% more dense at the interface between the polymer and the transport channels than within regions of the polymer not abutting a transport channel.

The density of probe molecule in a network can be verified using the following procedure:

The network is brought into contact with an aqueous liquid at room temperature, for example, in a bowl. The liquid contains a plurality of nanoparticles attached to a moiety that interacts with the probe molecules in the network, for example streptavidin if the probe molecules are biotinylated. The size of the nanoparticles is smaller than the mesh size of the network and smaller than the minimum cross-section of at least one type of transport channel in the network to allow the nanoparticles to become distributed throughout the polymer. Suitable nanoparticles are quantum dots 2-5 nanometers in dimeter.

An incubation period is selected so that the network in the liquid is completely hydrated, i.e., that the network on average takes the same amount of water as it releases. The incubation period can be, for example, one hour. The penetration of the nanoparticles in the network can be accelerated by setting in motion the network and/or the liquid during the incubation, for example, by vibrating the network and/or liquid, preferably by means of ultrasonic waves.

After completion of the incubation, the liquid is separated from the network, for example, by draining the liquid from the bowl or taking the network out of the bowl.

Then, the hydrated network is frozen, for example, by means of liquid nitrogen. Thereafter, the frozen network can be cut with the aid of a cryomicrotome along mutually parallel cutting planes into thin slices. The cutting planes are arranged transversely to the longitudinal extension of the transport channel and penetrate the transport channel. The cutting is preferably carried out using a liquid nitrogen-cooled diamond blade. The thickness of the slices can be, for example, about 100 nm or 200 nm.

With the aid of a microscope, the nanoparticles disposed in the disks obtained by cutting the frozen network are located. The nanoparticles can be fluorescent and optically highlighted so that they can be better distinguished from the network, if necessary. The locating of the nanoparticles can be done using a suitable software with image processing methods. To examine the disks, preferably a confocal microscope laser scanning microscope with fluorescence optics or an electron microscope is used.

The geometry and/or position information of the nanoparticles obtained in this manner may be, with the aid of a computer, used to make a three-dimensional geometric model of distribution of the nanoparticles in the network. The model can then be used to determine whether the distribution of nanoparticles reflects a greater density of probe molecules near sites of transport channels.

5.2. Arrays

The three-dimensional networks of the disclosure can be positioned (e.g., deposited) on a substrate, and are preferably immobilized on a substrate (e.g., by covalent cross-links between the network and the substrate). A plurality of networks can be immobilized on a substrate to form an array useful, for example, as a biochip.

Suitable substrates include organic polymers, e.g., cycloolefin copolymers (COCs), polystyrene, polyethylene, polypropylene, polycarbonate, and polymethylmethacrylate (PMMA, Plexiglas®). Ticona markets an example of a suitable COC under the trade name Topas®. Inorganic materiels (e.g., metal, glass) can also be used as a substrate. Such substrates can be coated with organic molecules to allow for cross-links between the network and a surface of the substrate. For example, inorganic surfaces can be coated with self-assembled monolayers (SAMs). SAMs can themselves be completely unreactive and thus comprise or consist of, for example, pure alkyl silanes. Other substrates can also be suitable for cross-linking to the three-dimensional network provided they are able to enter into stable bonds with organic molecules during free-radical processes (e.g., organoboron compounds).

The substrate can be rigid or flexible. In some embodiments, the substrate is in the shape of a plate (e.g., a rectangular plate, a square plate, a circular disk, etc.). For example, the substrate can comprise a microwell plate, and the three-dimensional networks can be positioned in the wells of the plate.

Figure 8:
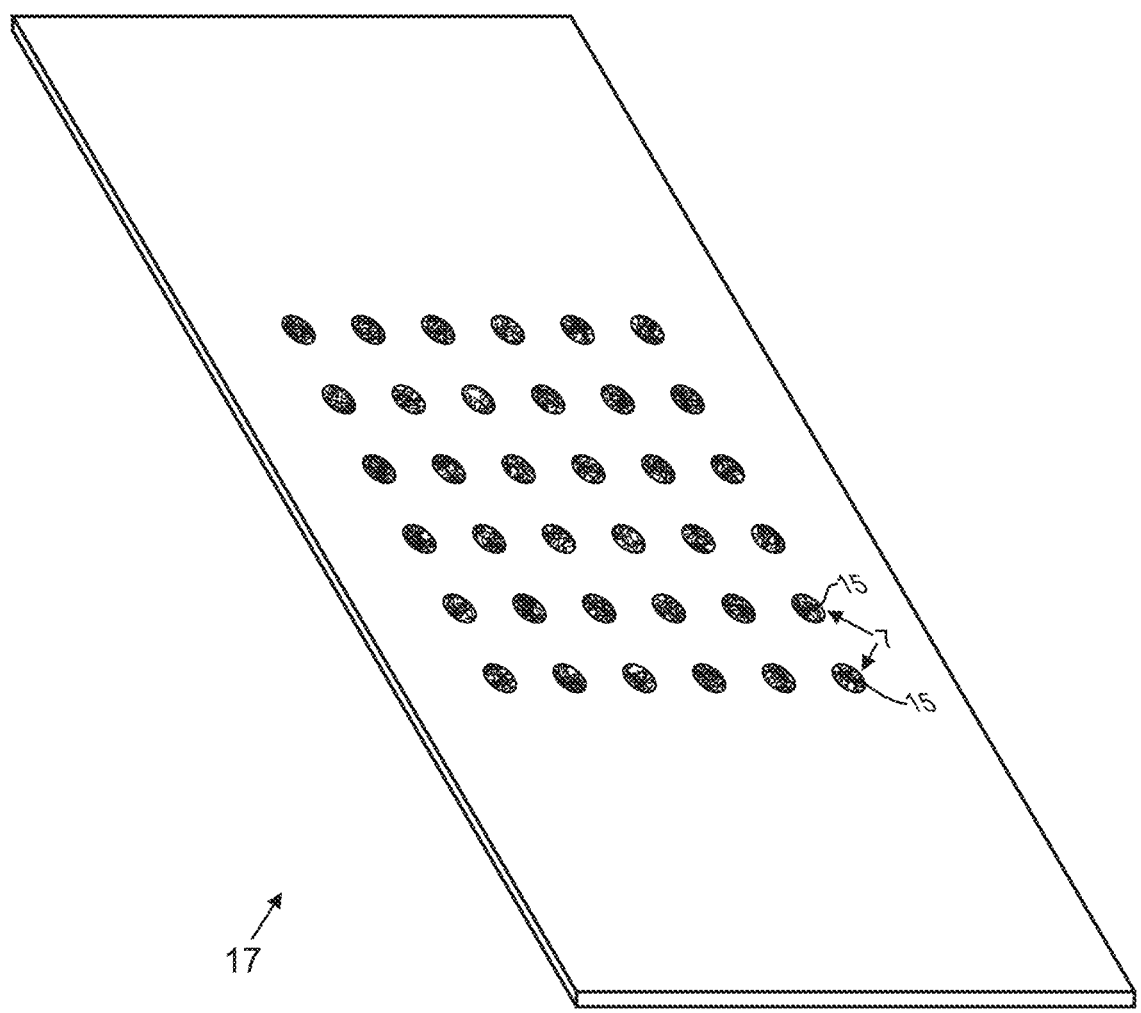
FIG. 8 shows a perspective view of a biochip (17) on which polymer networks (15) are located at spots (7) arranged as a matrix of rows and columns. The chip preferably has an organic surface.
Figure 9:
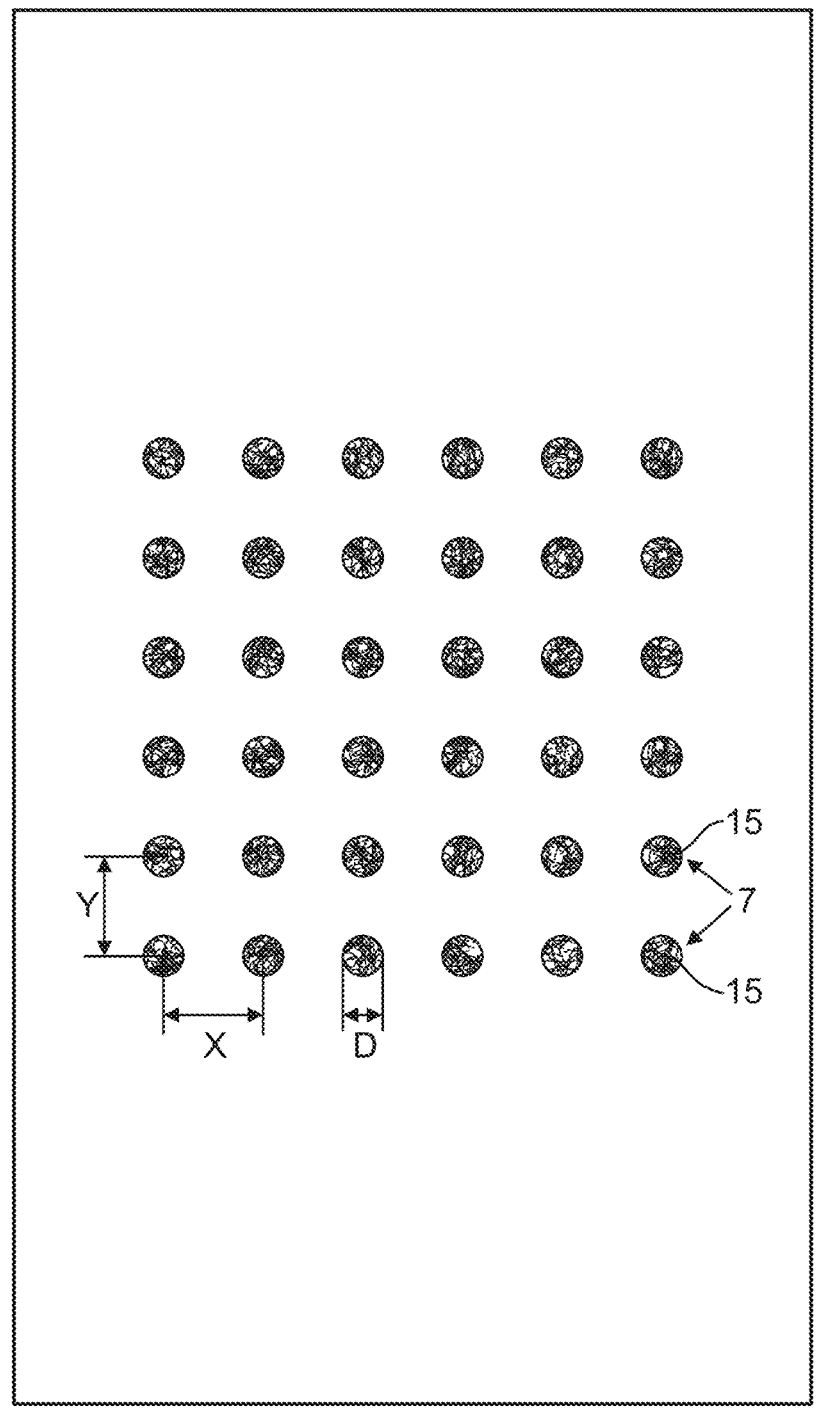
FIG. 9 shows a top view of a biochip (17) as shown in FIG. 8, where each polymer network (15) has a diameter (D), and where the rows and columns are separated by a distance Y and a distance X, respectively, measured from the center points of the polymer networks (15).

The individual networks can be positioned at distinct spots on a surface of the substrate, e.g., in a matrix comprising a plurality of columns and rows. In the embodiment shown in FIG. 8, the networks are located at 36 spots arranged in six columns and six rows. Arrays having different numbers of rows and columns, the number of each of which can be independently selected, are contemplated (e.g., 2 to 64 columns and 2 to 64 rows). The columns can be separated by a distance X and the rows can be separated by a distance Y (for example, as shown in FIG. 9) so as to form a grid of spots on which the individual networks can be located. X and Y can be selected so that the networks, located at the spots of the grid, do not contact each other in the dehydrated state and do not contact each other in the hydrated state. The dimensions X and Y can be the same or different. In some embodiments, X and Y are the same. In some embodiments, X and Y are different. In some embodiments, X and Y are independently selected from distances of at least about 500 µm (e.g., 500 µm to 5 mm, 500 µm to 4 mm, 500 µm to 3 mm, 500 µm to 2 mm, or 500 µm to 1 mm). In some embodiments, X and Y are both about 500 µm. In other embodiments, X and Y are both 500 µm.

Figure 10:
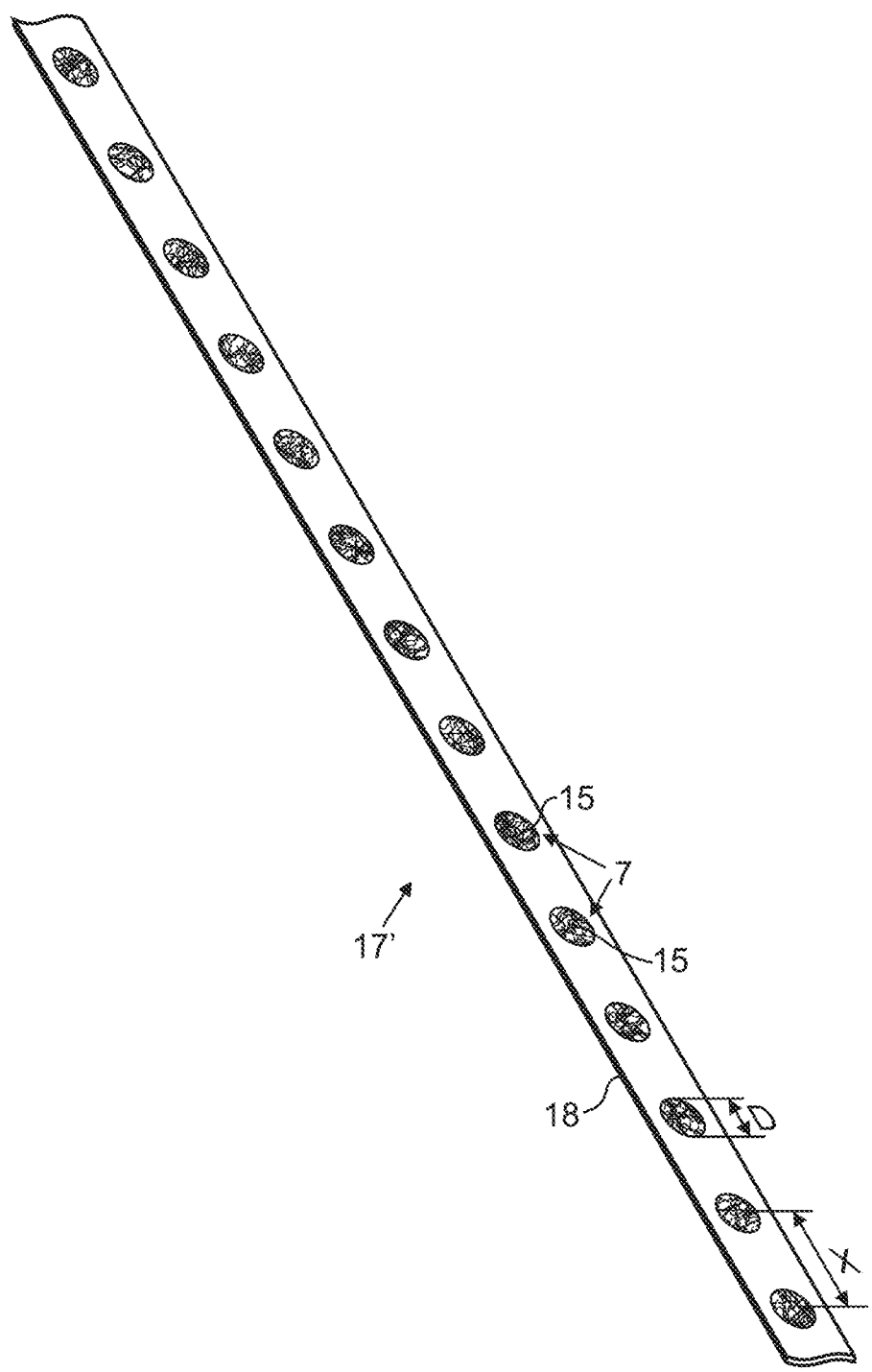
FIG. 10 shows a biosensor (17') comprising a flexible substrate band (18) on which polymer networks (15) having a diameter (D) are located at spots (7) separated by distance X measured from the center points of the polymer networks.

In some embodiments, substrate is band-shaped (for example, as shown in FIG. 10). The networks can be arranged as a single row extending in the longitudinal direction of a band-shaped organic surface, or can be arranged as multiple rows extending in the longitudinal direction of the band-shaped surface. The rows and columns in such band-shaped arrays can have grid dimensions X and Y as described above.

The individual networks can each cover an area of the surface of the array that is circular or substantially circular. Typically, the diameter of the area on the surface of the array covered by the individual networks (i.e., the spot diameter) is 80 µm to 1000 µm. In various embodiments, the spot diameter is 80 µm, 100 µm, 120 µm, 140 µm, 160 µm, 180 µm, 200 µm, 300 µm, 400 µm, 500 µm, 600 µm, 700 µm, 800 µm, 900 µm, or 1000 µm, or selected from a range bounded by any two of the foregoing embodiments, e.g., 80 µm to 200 µm, 100 µm to 120 µm, 120 µm to 140 µm, 120 µm to 180 µm, 140 µm to 160 µm, 160 µm to 180 µm, 180 µm to 200 µm, 120 µm to 200 µm, 100 µm to 400 µm, 160 µm to 600 µm, or 120 µm to 700 µm, and so on and so forth. In a preferred embodiment, the diameter ranges from 100 µm to 200 µm or a subrange thereof.

The arrays of the disclosure typically have at least 8 individual three-dimensional networks. In certain aspects, the arrays have at least 16, at least 24, at least 48, at least 96, at least 128, at least 256, at least 512, or at least 1024 individual three-dimensional networks. In some embodiments, the arrays of the disclosure have 24, 48, 96, 128, 256, 512, 1024, 2048, 4096 or 8192 individual networks, or have a number of three-dimensional networks selected from a range bounded any two of the foregoing embodiments, e.g., from 8 to 128, 8 to 512, 24 to 8192, 24 to 4096, 48 to 2048, 96 to 512, 128 to 1024, 24 to 1024, 48 to 512, 96 to 1024, or 128 to 512 three-dimensional networks, and so on and so forth. In a preferred embodiment, number of three-dimensional networks on an array ranges from 8 to 1024. In a particularly preferred embodiment, the number of three-dimensional networks on an array ranges from 25 to 400.

The individual networks which comprise the arrays of the disclosure can have identical or different probes (e.g., each network can have a unique set of probes, multiple networks can have the same set of probes and other networks can have a different set or sets of probes, or all of networks can have the same set of probes). For example, networks arranged in the same row of a matrix can comprise the same probes and the networks arranged in different rows of the matrix can have different probes.

Typically, the individual networks on an array vary by no more than 20%, no more than 15%, no more than 10% or no more than 5% from one another by spot diameter and/or network volume.

In some embodiments, the arrays comprise one or more individual networks (e.g., spots on an array) with one or more control oligonucleotides or probe molecules. The control oligonucleotides can be labelled, e.g., fluorescently labelled, for use as a spatial control (for spatially orienting the array) and/or a quantifying the amount of probe molecules bound to the networks, for example, when washing and reusing an array of the disclosure (i.e., as a "reusability control"). The spatial and reusability control probes can be the same or different probes.

The same spot on the array or a different spot on the array can further include an unlabelled probe that is complementary to a known target. When used in a hybridization assay, determining the signal strength of hybridization of the unlabelled probe to the labelled target can determine the efficiency of the hybridization reaction. When an individual network (i.e., a spot on an array) is used both as a reusability and/or spatial control and a hybridization control, a different fluorescent moiety can be used to label the target molecule than the fluorescent moiety of the reusability control or spatial control probes.

In some embodiments, the arrays of the disclosure can be reused at least 5 times, at least 10 times, at least 20 times, at least 30 times, at least 40 times, or at least 50 times (e.g., 5 to 20 times, 5 to 30 times, 10 to 50 times, 10 to 20 times, 10 to 30 times, 20 to 40 times, or 40 to 50 times, preferably comprising reusing the array 10 to 50 times). The array can be washed with a salt solution under denaturating conditions (e.g., low salt concentration and high temperature). For example, the array can be washed with a 1-10 mM phosphate buffer at 80-90° C. between uses. The temperature of the wash can be selected based upon the length (Tm) of the target:probe hybrid.

The integrity of an array can be determined by a "reusability control" probe. The reusability control probe can be fluorescently labeled or can be detected by hybridization to a fluorescently labeled complementary nucleic acid. The fluorescent label of a fluorescently labeled reusability control probe may be bleached by repeated excitation, before the integrity of the nucleic acid is compromised; in such cases any further reuses can include detection of hybridization to a fluorescently labeled complementary nucleic acid as a control. Typically, an array of the invention is stable for at least 6 months.

In various embodiments, a fluorescently labeled reusability control probe retains at least 99%, 95% 90%, 80%, 70%, 60%, or 50% of its initial fluorescence signal strength after 5, 10, 20, 30, 40, or 50 uses. Preferably, the reusability control probe retains least 75% of its fluorescence signal strength after 5 or 10 uses. An array can continue to be reused until the reusability control probe retains at least 50% of its fluorescence signal strength, for example after 20, 30, 40 or 50 reuses. The fluorescent signal strength of the control probe can be tested between every reuse, every other reuse, every third reuse, every fourth reuse, every fifth reuse, every sixth reuse, every seventh reuse, every eighth reuse, every ninth reuse, every tenth reuse, or a combination of the above. For example, the signal strength can be tested periodically between 5 or 10 reuses initially and the frequency of testing increased with the number of reuses such that it is tested after each reuse after a certain number (e.g., 5, 10, 20, 30, 40 or 50) uses. In some embodiments, the frequency of testing averages once per 1, 1.5, 2, 2.5, 3, 4, 5 or 10 uses, or averages within a range bounded between any two of the foregoing values, e.g., once per 1-2 uses, once per 1-1.5 uses, once per 1-3 uses, or once per 1.5-3 uses.

It is noted that the nomenclature of "spatial control", "reusability control" and "hybridization control" is included for convenience and reference purposes and is not intended to connote a requirement that the probes referred to "spatial control", "reusability control" and "hybridization control" be used as such.

5.3. Processes for Making Three-Dimensional Polymer Networks

In one aspect, the processes of the disclosure for making three-dimensional polymer networks comprise (a) exposing a mixture comprising an aqueous salt solution, a polymer, a cross-linker and, optionally, one or more probes to salt crystal forming conditions, (b) exposing the mixture to cross-linking conditions to cross-link the polymer for form a cross-linked polymer network, and (c) contacting the cross-linked polymer network with a solvent to dissolve the salt crystals and form one or more transport channels.

The processes can further comprise a step of forming the mixture by combining an aqueous salt solution, a polymer, a cross-linker and, optionally, one or more probes, and/or further comprise a step of applying the mixture to a substrate (e.g., a substrate described in Section 5.2) prior to exposing the mixture to salt crystal forming conditions. If the polymer being used has a pre-attached cross-linker (e.g., when using a copolymer polymerized from a monomer comprising a cross-linker), the step of forming the mixture can comprise combining an aqueous salt solution with the polymer and, optionally, one or more probes.

The mixture can be applied to a substrate prior to exposing the mixture to salt crystal forming conditions for example, by spraying the mixture onto a surface of the substrate (e.g., at 1024 sites on the surface). The mixture can be applied to the surface using a DNA chip spotter or inkjet printer, for example. In a preferred embodiment, the mixture is sprayed using an inkjet printer. This permits a simple and rapid application of the mixture to a large number of spots on the substrate. The spots can be arranged, for example, in the form of a matrix in several rows and/or columns. Preferably, the salt content in the mixture during printing is below the solubility limit so that the mixture does not crystallize in the printing head of the printer. The volume of mixture applied at individual spots can be, for example, 100 pl, 200 pl, 300 pl, 400 pl, 500 pl, 750 pl, 1 nl, 2 nl, 3 nl, 4 nl, or 5 nl, or can be selected from a range bounded by any two of the foregoing values (e.g., 100 pl to 5 nl, 100 pl to 1 nl, 300 pl to 1 nl, 200 pl to 750 nl, 100 pl to 500 pl, 200 pl to 2 nl, 500 pl to 2 nl 1 nl to 2 nl, and so on and so forth). In preferred embodiments, the spot volume is 200 pl to 4 nl.

The diameter of the individual spots will depend on the composition of the mixture, the volume of the mixture applied, and the surface chemistry of the substrate. Spot diameters typically range between 80 µm to 1000 µm and can be obtained by varying the foregoing parameters. In various embodiments, the spot diameters are 80 µm, 100 µm, 120 µm, 140 µm, 160 µm, 180 µm, 200 µm, 300 µm, 400 µm, 500 µm, 600 µm, 700 µm, 800 µm, 900 µm, or 1000 µm, or selected from a range bounded by any two of the foregoing embodiments, e.g., 80 µm to 200 µm, 100 µm to 120 µm, 120 µm to 140 µm, 120 µm to 180 µm, 140 µm to 160 µm, 160 µm to 180 µm, 180 µm to 200 µm, 120 µm to 200 µm, 100 µm to 400 µm, 160 µm to 600 µm, or 120 µm to 700 µm, and so on and so forth. In a preferred embodiment, the diameter ranges from 100 µm to 200 µm or a subrange thereof.

Suitable polymers, cross-linkers, and probes that can be used in the processes of the disclosure are described in Sections 5.1.1, 5.1.2, and 5.1.4, respectively. In some embodiments, the polymer used in the processes has at least one cross-linker group per polymer molecule. In a preferred embodiment, the polymer has at least two cross-linker groups per molecule. In a particularly preferred embodiment, the polymer has at least two photoreactive cross-linker groups per molecule. In these embodiments, separate polymer and cross-linker molecules are not needed.

Suitable salts that can be included in the mixture are described in Section 5.3.1. Suitable salt crystal forming conditions are described in Section 5.3.2. Suitable cross-linking conditions are described in Section 5.3.3. Suitable solvents for dissolving the salt crystals are described in Section 5.3.4.

5.3.1. Salt

The polymer networks of the disclosure are characterized by transport channels that result when the polymers are cross-linked in a mixture containing salt crystals formed from an aqueous solution containing at least two types of salts.

The salts are preferably selected for their compatibility with one or more probes. Ideally, each salt has one or more of the following characteristics, (i) the salt is not toxic to the probes (e.g., the salt does not denature the probes), (ii) the salt does not react chemically with the probes, (iii) the salt does not attack fluorophores, such as cyanine dyes, which are suitable for the optical marking of probes, and/or (iv) the salt does not react with analytes, detection molecules, and/or binding partners bonded thereto. Preferably, at least one of the salts forms needle-shaped crystals.

In a preferred embodiment, the aqueous salt solution comprises at least two types of monovalent cations, for example two types of alkali metal cations. Alkali metal cations that can be used include sodium cations and potassium cations, although other alkali metal cations, such as lithium cations, can also be used.

For optimal signal:noise ratio for detection of nucleic acid analytes, the aqueous salt solution preferably comprises sodium and potassium cations and/or has a total monovalent cation concentration such that when combined with the polymer solution and optional probe solution (prior to cross-linking) the resulting mixture has a total monovalent cation concentration of at least 500 mM. In particular embodiments, the sodium ion concentration in the mixture is at least 250 mM, and may range from 250 mM to 500 mM, more preferably is in the 300 mM to 400 mM range. In a specific embodiment, the sodium ion concentration in the mixture is 350 mM. The potassium ion concentration in the mixture is preferably at least 150 mM, and preferably is in the range of 150 mM to 500 mM, more preferably is in the range of 200 mM to 400 mM, and yet more preferably is in the range of 250 mM to 350 mM.

The aqueous salt solution can be made using a disodium hydrogen phosphate ($Na_2HPO_4$) and/or sodium dihydrogen phosphate ($NaH_2PO_4$) which, in aqueous solution, releases $Na^+$ cations and phosphate ions $PO_4^{3-}$. The aqueous salt solution can also be made using dipotassium hydrogen phosphate ($K_2HPO_4$) and/or potassium dihydrogen phosphate ($KH_2PO_4$).

Preferably, the aqueous salt solution can be a sodium phosphate buffer containing both disodium hydrogen phosphate and sodium dihydrogen phosphate, supplemented with dipotassium hydrogen phosphate ($K_2HPO_4$) and/or potassium dihydrogen phosphate ($KH_2PO_4$). In one embodiment, a sodium phosphate buffer containing both disodium hydrogen phosphate and sodium dihydrogen phosphate and a potassium phosphate buffer containing both dipotassium hydrogen phosphate and potassium dihydrogen phosphate are made separately and combined into a single aqueous solution, prior to or after mixing with the polymer and/or probe solutions.

Generally, the aqueous salt solution preferably has a pH ranging from 6 to 9, and more preferably in the range of 7-8.5. In certain exemplary embodiments, the pH is 7.5, 8, or 8.5, most preferably 8.

For networks containing protein-based probe biomolecules, the aqueous salt solution can include phosphate buffered saline ("PBS") and/or a monovalent cation sulfate.

5.3.2. Salt Crystal Forming Conditions

Salt crystal forming conditions can comprise dehydrating the mixture or cooling the mixture until the relative salt content in the mixture increases to above the solubility limit, meaning that the mixture is supersaturated with the salt. This promotes the formation of salt crystals from a crystallization germ located in the volume of the mixture towards the surface of the mixture. It is believed, without being bound by theory, that the use of aqueous solutions containing at least two different monovalent metal ions results in the formation of at least two different types of salt crystals.

The mixture can be dehydrated by heating the mixture, exposing the mixture to a vacuum, and/or reducing the humidity of the atmosphere surrounding the mixture.

The mixture can be heated by placing the mixture on a heated substrate or surface (e.g., between about 50° C. to about 70° C.), heating the substrate or surface on which the mixture has been placed (e.g., to between about 50° C. to about 70° C.), and/or contacting the mixture with a hot gas (e.g., air, nitrogen, or carbon dioxide having a temperature that is higher than the temperature of the mixture) such that water is evaporated from the mixture. The contacting with the hot gas can, for example, take place by placing the mixture in a heating oven. During the transportation to the heating oven, the mixture can be kept at a humidity of 40% or greater, for example at a relative humidity of approximately 60%, although higher relative humidities, even as high as 75% or greater, are also feasible. Mixtures with higher potassium ion concentrations can tolerate lower relative humidities, and mixtures with lower potassium salt concentration are preferably kept at higher relative humidities during transport.

By heating the mixture it is also possible to activate thermally activatable cross-linkers, if present, and cross-link the polymer thereby.

In some embodiments, the temperature of the heated substrate and/or air used to dehydrate the mixture is 20° C. or more above the temperature of the mixture before heating the mixture, but less than 100° C.

The mixture can be cooled by placing the mixture on a cooled substrate or surface (e.g., between about 5° C. to about 15° C.), cooling the substrate or surface on which the mixture has been placed (e.g., to between about 5° C. to about 15° C.) and/or bringing it into contact with a cold gas (e.g., air, nitrogen, or carbon dioxide having a temperature that is lower than the temperature of the mixture). When cooled, the temperature-dependent solubility limit of the salt in the mixture decreases until the mixture is ultimately supersaturated with the salt. In some embodiments, the mixture is cooled by incubating it in a cold chamber with low humidity (e.g., temperatures between 0° C. and 10° C., relative humidity<40%).

The temperature in the mixture is preferably held above the dew point of the ambient air surrounding the mixture during the formation of the one or more salt crystals. This prevents the mixture becoming diluted with water condensed from the ambient air, which could lead to a decrease in the relative salt content in the mixture.

5.3.3. Cross-Linking Conditions

The cross-linking conditions can be selected based upon the type of cross-linker used. For example, when using a cross-linker activated by ultraviolet light (e.g., benzophenone, a thioxanthone or a benzoin ether), the cross-linking conditions can comprise exposing the mixture to ultraviolet (UV) light. In some embodiments, UV light having a wavelength from about 250 nm to about 360 nm is used (e.g., 260±20 nm or 355±20 nm). The use of lower energy/longer wavelength UV light (e.g., 360 nm UV light vs. 254 nm UV light) can require longer exposure times. When using a cross-linker activated by visible light (e.g., ethyl eosin, eosin Y, rose bengal, camphorquinone or erythirosin), the cross-linking conditions can comprise exposing the mixture to visible light. When using a thermally activated cross-linker (e.g., 4,4' azobis(4-cyanopentanoic) acid, and 2,2-azobis[2-(2-imidazolin-2-yl) propane] dihydrochloride, or benzoyl peroxide), the cross-linking conditions can comprise exposing the mixture to heat.

The length and intensity of the cross-linking conditions can be selected to effect cross-linking of polymer molecules to other polymer molecules, cross-linking of polymer molecules to probe molecules (if present), and cross-linking of polymer molecules to substrate molecules or organic molecules present on the substrate (if present). The length and intensity of cross-linking conditions for a mixture containing probes can be determined experimentally to balance robustness of immobilization and nativity of probe molecules, for example.

5.3.4. Salt Crystal Dissolution

After cross-linking the polymer, the salt crystals can be dissolved in the solvent in such a way that at least one transport channel is formed in the network. It is believed, without being bound by theory, that the use of two types of monovalent salt cations during crystal formation results in at least two types of crystals, compact crystals and a needle-shaped crystals. The dissolution of the compact crystals is believe to result in short channels that create a sponge-like effect in the network, pierced by long channels resulting from the dissolution of the needle-shaped crystals.

When using an array produced by the method of the disclosure as a biological sensor, a high measurement accuracy and high measurement dynamic are permitted.

The solvent for dissolving the one or more salt crystals can be chosen in such a way that it is compatible to the polymer and probes, if present (e.g., the solvent can be chosen such that it does not dissolve the polymer and probes). Preferably, the solvent used is a water based buffer, such as diluted phosphate buffer. Methanol, ethanol, propanol or a mixture of these liquids can be added to the buffer to facilitate the removal of unbound polymer from the network.

After the removal of the salt crystals the network can collapse due to drying and can be rehydrated. Drying the network has advantages for shipping and stabilization of probe biomolecules.

5.3.5. Methods of Using the Three-Dimensional Networks

The networks and arrays of the disclosure can be used to determine the presence or absence of an analyte in a sample, preferably a liquid sample. The disclosure therefore provides methods for determining whether an analyte is present in a sample or plurality of samples, comprising contacting a network or array of the disclosure comprising probe molecules that are capable of binding to the analyte with the sample or plurality of samples and detecting binding of the analyte to the probe molecules, thereby determining whether the analyte is present in the sample or plurality of samples. When arrays comprising different species of probes capable of binding different species of analyte are used in the methods, the presence of the different species of analytes can be determined by detecting the binding of the different species of analytes to the probes. In some embodiments, the methods further comprise a step of quantifying the amount of analyte or analytes bound to the array.

The analyte can be, for example, a nucleic acid, such as a polymerase chain reaction (PCR) amplicon. In some embodiments, the PCR amplicon is amplified from a biological or environmental sample (e.g., blood, serum, plasma, tissue, cells, saliva, sputum, urine, cerebrospinal fluid, pleural fluid, milk, tears, stool, sweat, semen, whole cells, cell constituent, cell smear, or an extract or derivative thereof). In some embodiments, the nucleic acid is labeled (e.g., fluorescently labeled).

An analyte placed on the surface of the network can penetrate into the interior of the network through the transport channel in order to specifically bind to a probe (e.g., a biomolecule) covalently bonded there to the polymer. When using the arrays of the disclosure with the networks immobilized thereon as biological sensor, a high measurement accuracy and also a high measurement dynamic is permitted.

The networks and arrays of the disclosure can be regenerated after use as a biosensor and can be used several times (e.g., at 5 times, at least 10 times, at least 20 times, at least 30 times, at least 40 times, or at least 50 times). If the probe molecules are DNA, this can be achieved, for example, by heating the network(s) in an 1× phosphate buffered saline to a temperature between 80° C. and 90° C. for about 10 minutes. Then, the phosphate buffered saline can be exchanged for a new phosphate buffered saline to wash the denatured DNA out of the network(s). If the probe molecules of the network(s) or array are antigens the network(s) or array can be regenerated by bringing the network(s) into contact with 0.1 N NaOH for about 10 minutes. Then, the 0.1 N NaOH can be exchanged for a phosphate buffered saline to wash the antigens out of the network. Thus, some embodiments of the methods of using the networks and arrays of the disclosure comprise using a network or array that has been washed prior to contact with a sample or a plurality of samples.

5.4. Applications of Arrays of the Disclosure

Because the arrays of the invention achieve economical determination of the qualitative and quantitative presence of nucleic acids in a sample, it has immediate application to problems relating to health and disease in human and non-human animals.

In these applications a preparation containing a target molecule is derived or extracted from biological or environmental sources according to protocols known in the art. The target molecules can be derived or extracted from cells and tissues of all taxonomic classes, including viruses, bacteria and eukaryotes, prokaryotes, protista, plants, fungi, and animals of all phyla and classes. The animals can be vertebrates, mammals, primates, and especially humans. Blood, serum, plasma, tissue, cells, saliva, sputum, urine, cerebrospinal fluid, pleural fluid, milk, tears, stool, sweat, semen, whole cells, cell constituent, and cell smears are suitable sources of target molecules.

The target molecules are preferably nucleic acids amplified (e.g., by PCR) from any of the foregoing sources).

The arrays of the invention can include probes that are useful to detect pathogens of humans or non-human animals. Such probes include oligonucleotides complementary at least in part to bacterial, viral or fungal targets, or any combinations of bacterial, viral and fungal targets.

The arrays of the invention can include probes useful to detect gene expression in human or non-human animal cells, e.g., gene expression associated with a disease or disorder such as cancer, cardiovascular disease, or metabolic disease for the purpose of diagnosing a subject, monitoring treatment of a subject or prognosis of a subject's outcome. Gene expression information can then track disease progression or regression, and such information can assist in monitoring the success or changing the course of an initial therapy.

6. EXEMPLARY PROTOCOLS

The following exemplary protocols, which refer to the reference numbers provided in the figures, are within the scope of the disclosure and can be used in conjunction with the polymers, cross-linkers and probes of Sections 5.1.1, 5.1.2 and 5.1.4, respectively. Further useful polymers (including co-polymers) and cross-linker groups for use in the following methods are described in Rendl et al., 2011, Langmuir 27:6116-6123 and in US 2008/0293592, the contents of which are incorporated by reference herein. In one embodiment, a polymer mixture according to Section 7.2 is used.

6.1. Exemplary Protocol 1

Figure 1:
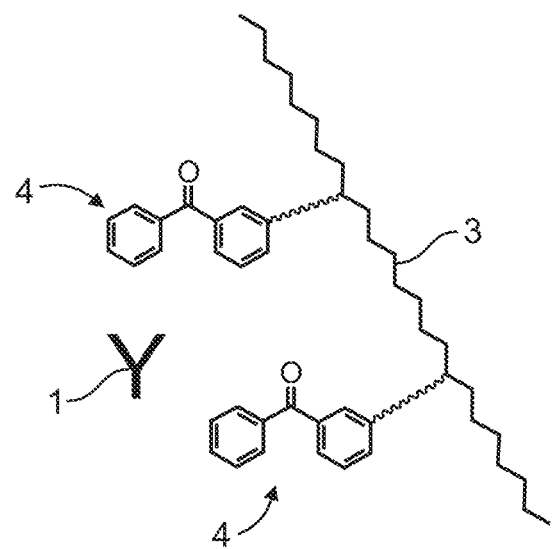
Figure 2:
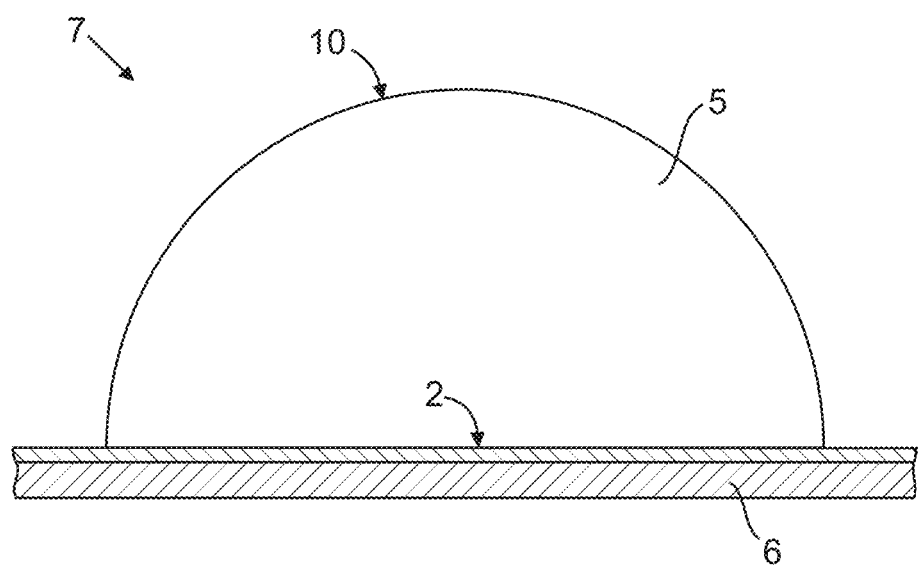
Figure 3:
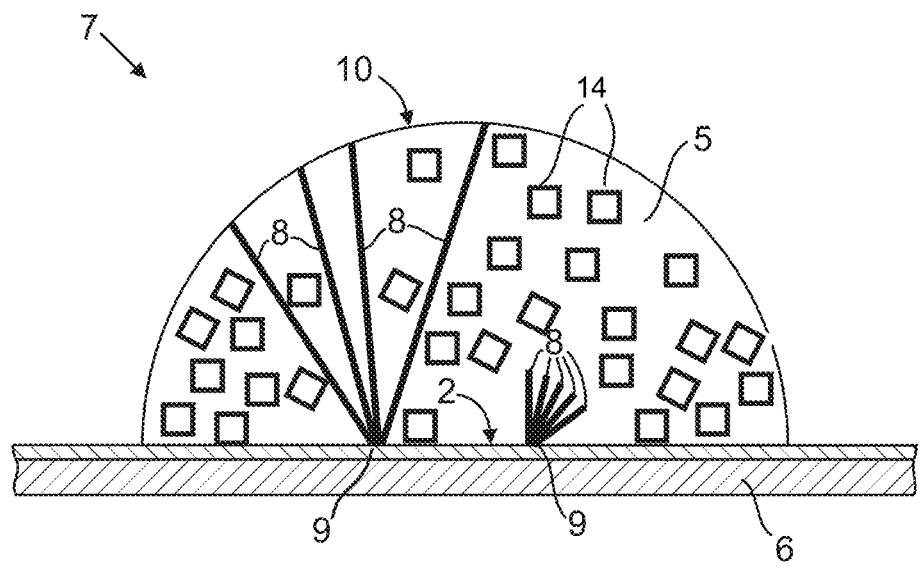
FIG. 3 shows shows a cross-section through the arrangement shown in FIG. 2 after the mixture has been heated and both (a) needle-shaped salt crystals (8) extending from crystallization germs (9) and (b) compact crystals (14) have been formed in the salt solution.
Figure 4:
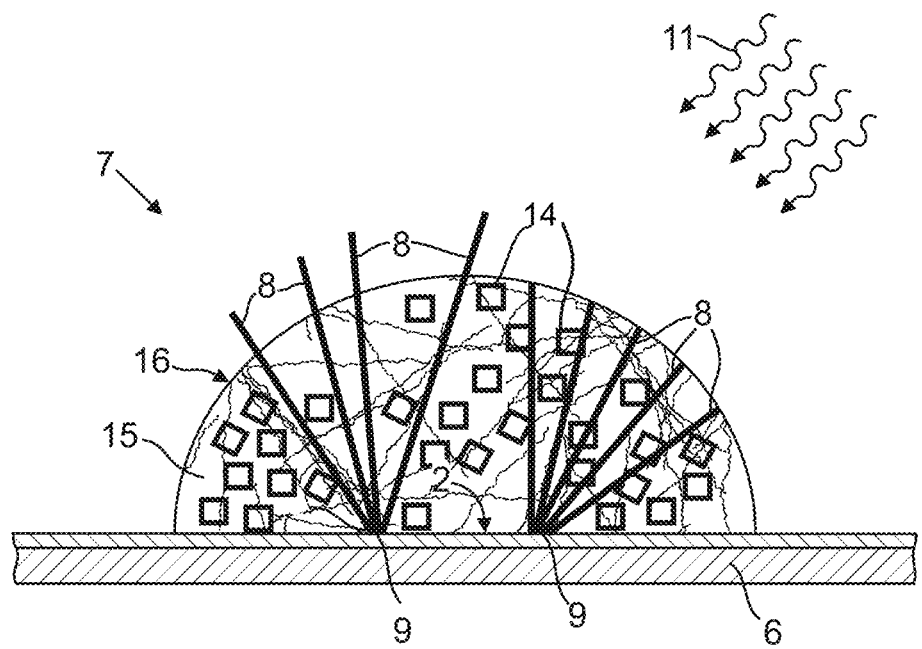
FIG. 4 shows shows a cross-section through the arrangement shown in FIG. 3 after the mixture has been dried and irradiated with optical radiation (11) to form a polymer network (15) having a surface (16).
Figure 5:
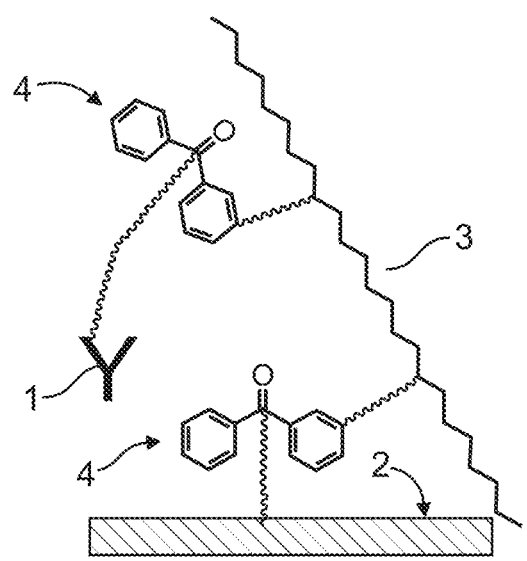
FIG. 5 shows shows a diagrammatic representation of the mixture of FIG. 1 following irradiation with optical radiation.

A plate with a surface (2) that is preferably organic is placed on a holder (6) that is heated. Temperatures between 50° C. and 70° C. are suitable. A mixture (5) containing a polymer (3), probe biomolecules (1) and an aqueous salt solution is spotted on the organic surface (2) using a standard DNA chip spotter (e.g., Scienion, Germany). Volumes of 0.5 to 4 nl are printed on each spot (7) (see, FIG. 2). The liquid of these spots dries almost immediately leading to a nucleation of salt crystals (8), (14). After nucleation, needle-shaped salt crystals can extend from at least one crystallization germ (9) located in the volume of the mixture (5) to the surface (10) of the mixture (5) (see, FIG. 3). Additionally, the formation of shorter cubic or rod-shaped crystals (14) is believed to occur (see, FIG. 3). After nucleation of the crystals (8), (14), the spots (7) are irradiated in a UV cross-linker immediately with optical UV radiation (11) (see, FIG. 4) such that the probe biomolecules (1) are covalently bonded to the polymer (3), and the polymer (3) is covalently bonded to the organic surface (2) and cross-linked (see, FIG. 5). Care is taken that the dried, cross-linked mixture (5) is not attracting moisture to become liquid again.

Figure 6:
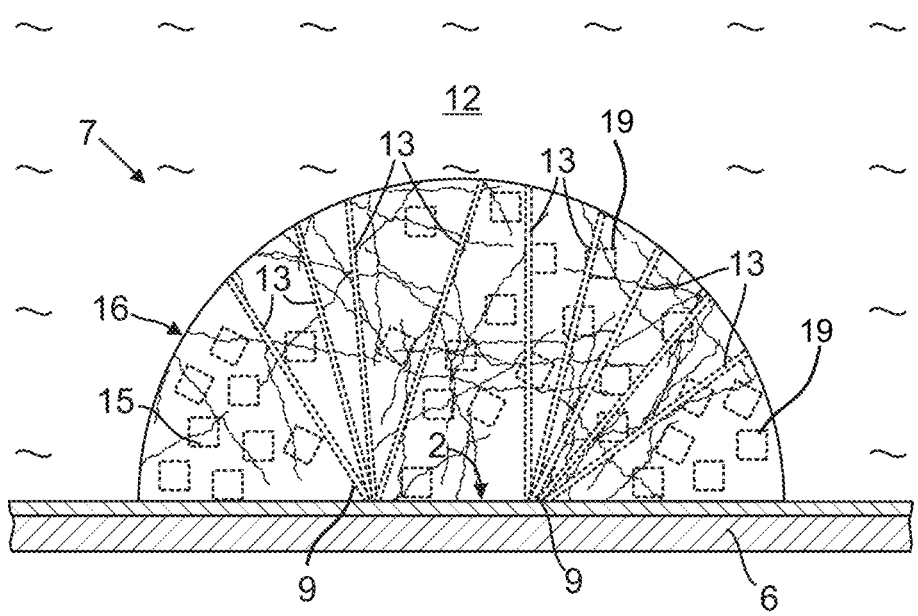
FIG. 6 shows shows a cross-section through the arrangement shown in FIG. 4 after dissolving the salt crystals in a solvent (12), forming transport channels in the form of long channels (13) and short channels (19).

The dried, cross-linked mixture (5) is then brought into contact with a solvent (12) for the crystals (8) such that at the places at which the crystals (8), (14) were, long (13) and short (19) channels are formed in the network (15) comprising the polymer (3) and the probe biomolecules (1) (see, FIG. 6). Thereafter, the solvent (12) is removed. The long channels (13) can extend from the surface (16) of the network (15) into the interior of the network (15). The solvent (12) in which the salt crystals (8), (14) are dissolved is chosen in such a way that it is compatible to the probe biomolecule (1) and also the polymer (3). Preferably, the solvent (12) used is water based.

6.2. Exemplary Protocol 2

A mixture (5) containing a polymer (3), probe biomolecules (1) and an aqueous salt solution is spotted on an organic surface (2) arranged on a plate using a standard DNA chip spotter (e.g., Scienion, Germany). Volumes of 0.5 to 4 nl are printed on each spot (7) (see, FIG. 2). The plate with the spots (7) on the surface (2), preferably organic, is placed on a holder (6) that is chilled (see, FIG. 3). Temperatures between 5° C. and 15° C. are suitable. The liquid of these spots is cooled down to reach an over saturation of the buffer that almost immediately leads to a nucleation of crystals. After nucleation needle-shaped salt crystals (8) can extend from at least one crystallization germ (9) located in the volume of the mixture (5) to the surface (10) of the mixture (5). Additionally, the formation of shorter cubic or rod-shaped crystals (14) is believed to occur (see, FIG. 3). After printing these targets are put in an oven (e.g., at 70° C.) for complete drying. After nucleation of the crystals the spots are irradiated in a UV cross-linker immediately with optical UV radiation (11) (see, FIG. 4) such that the probe biomolecules (1) are covalently bonded to the polymer (3), and the polymer (3) is covalently bonded to the organic surface (2) and cross-linked. Care is taken that the dried, cross-linked mixture is not attracting moisture to become liquid again.

The dried, cross-linked mixture (5) is then brought into contact with a solvent (12) to dissolve the crystals (8), (14) such that at the places at which the crystals (8), (14) were, transport channels, e.g., long channels (13) and short channels (19) are formed in the network (15) comprising the polymer (3) and the probe biomolecules (1). Thereafter, the solvent (12) is removed. The long channels (13) can extend from the surface (16) of the network (15) into the interior of the network (15). The solvent (12) in which the salt crystals (8), (14) are dissolved is chosen in such a way that it is compatible with the probe biomolecule (1) and the polymer (3). Preferably, the solvent (12) used is water based.

As can be seen in FIG. 6 a plurality of long channels (13) and short channels (19) can be formed in the network (15). The long channels (13) can extend from the surface (16) of the network (15) to at least one point located within the network (15). The long channels (13) can be arranged in such a way that—starting from the surface (16) in the direction of the interior—the lateral distance between the long channels (13) decreases.

6.3. Exemplary Protocol 3

A mixture (5) containing a polymer (3), probe biomolecules (1) and an aqueous salt solution is printed on a surface (2), preferably organic, of a plate at normal conditions with a humidity ranging from 40-80%, preferably 50-70%. The mixture can contain 350 mM sodium phosphate, pH 8, and 250-300 mM potassium phosphate, pH 8, for example. Volumes of 0.5 to 4 nl are printed on each spot (7). The moisture content in the print compartment makes sure the spots (7) stay liquid without crystal formation (i.e., no nucleation takes place). The plate is then put in a container, a cardboard box for example. Lids are put on the plate for transport. The plate with the spots (7) is then put in a drying oven or on a hot plate to rapidly cause nucleation such that needle-shaped salt crystals (8) extend from at least one crystallization germ (9) located in the volume of the mixture toward the surface (10) of the mixture (5). Additionally, the formation of shorter cubic or rod-shaped crystals (14) is believed to occur.

The temperature of the oven/hot plate should be 20° C. or more above the printing temperature. Temperatures above 100° C. are not necessary.

After drying, the mixture is irradiated to cross-link the polymer (3), probe biomolecules (1), and surface (2).

The dried, cross-linked mixture (5) is then brought into contact with a solvent (12) such that at the places at which the crystals (8), (14) were, long channels (13) and short channels (19) are formed in the network (15) comprising the polymer (3) and the probe biomolecules (1). Thereafter, the solvent (12) is removed. The long channels (13) can are extend from the surface (16) of the network (15) into the interior of the network (15). The solvent (12) in which the salt crystals (8), (14) are dissolved is chosen in such a way that it is compatible with the probe biomolecules (1) and the polymer (3). Preferably, the solvent (12) used is water based.

6.4. Exemplary Protocol 4

Alternatively, a plate with spots (7) on the surface (2), which is preferably organic, prepared as in exemplary protocol 3 can be cooled to achieve nucleation by putting in a cold chamber with low humidity (e.g., temperatures<10° C., relative humidity<40%). The drying can be performed by reducing the humidity or by applying a vacuum after nucleation has started. After nucleation, needle-shaped salt crystals (8) can extend from at least one crystallization germ (9) located in the volume of the mixture (5) toward the surface (10) of the mixture (5). Additionally, the formation of shorter cubic or rod-shaped crystals (14) is believed to occur. The plate with the spots (7) is put in an oven at 60°-70° C. for 1 hour to fully dry the spots. The spots (7) are UV irradiated with 1.00 J @ 254 nm in a UV cross-linker, i.e. Stratalinker 2400. To do this, the plate with the spots (7) can be put into the center of the chamber with the shorter side parallel to the door of the chamber. Then, the cover is removed and the cross-linker is started. When machine is finished the array is removed and the cover is replaced.

Alternatively, other UV cross-linkers with the same wavelength (240-270 nm, for example) or longer wavelengths, e.g., 360 nm, can be used.

The mixture (5) is then brought into contact with a solvent (12) to dissolve the crystals (8), (14) such that at the places at which the crystals (8), (14) were, long channels (13) and short channels (19) are formed in the network (15) comprising the polymer (3) and the probe biomolecules (1). Thereafter, the solvent (12) is removed. The long channels (13) can extend from the surface (16) of the network (15) into the interior of the network (15). The solvent (12) in which the salt crystals (8), (14) are dissolved is chosen in such a way that it is compatible with the probe biomolecules (1) the polymer (3). Preferably, the solvent (12) used is water based.

7. EXAMPLES 7.1. Background

Polymer networks made substantially as described herein but containing a buffer of sodium phosphate ("NaPi") at a concentration of 350 mM without a second salt can dry in and undergo phase separation if the humidity is not maintained at 60% or greater during drying on a heating plate. This is because at lower humidity levels crystallization can take place in an uncontrolled manner.

It would be desirable to increase the sodium phosphate concentration to avoid uncontrolled crystallization. However, the concentration of NaPi cannot be increased significantly as then NaPi crystals could precipitate in the printer and block the print nozzle.

Various salts (sodium chloride, sodium bwere used in combination with NaPi test experiments. But none of these gave better signals than the NaPi alone. Usually the hybridization signals of these spots were inferior (data not shown).

Other attempts to minimize drying in at normal humidity levels entailed testing phosphate buffered saline, sodium citrate bufer, or potassium phosphate buffer in lieu of NaPi led to lower hybridization signals in the polymer networks.

But when NaPi buffer was strengthened by potassium-phosphate buffer (as described in Section 7.2) a stabilization of the liquid spot was observed without signal loss, particularly when the potassium phosphate concentration was greater than 150 mM.

When these experiments were performed there was a surprising observation. At higher potassium phosphate levels (150 mM and more) the background signal ("noise") was reduced and at concentrations of 200 mM the noise almost entirely absent from hybridization reaction (as described in Section 7.3). The reason for this effect is most likely that the short channels result in a sponge-like polymer matrix that is pierced by long channels from the sodium phosphate. The combination of these two structures then improves not only the on-kinetics (hybridization) but also the off-kinetics (washing off unbound or weakly bound material). The lower background signal reduces the background signal and therefore improves the LOD (limit of detection) of any test performed using polymer networks made using both sodium phosphate and potassium phosphate.

7.2. Example 1: Formation of Three-Dimensional Polymer Networks

A 10 mg/ml polymer stock solution was prepared by dissolving 10 mg of the cross-linking polymer poly(dimethylacrylamide) co 5% Methacryloyl-Benzophenone co 2.5% Sodium 4-vinylbenzenesulfonate in 1.0 ml of DNAse free water. This was achieved by vigorous shaking and vortexing for approximately 5 minutes until all the visible polymer is dissolved. The stock solution was then wrapped in foil to protect it from light and placed in a refrigerator overnight to ensure the polymer completely dissolves and to allow the foam to reduce. The polymer has at least two photoreactive groups per molecule.

Various mixtures containing 10 mg/ml of the polymer (PDMAA-5% MABP-2.5% SSNa), probe biomolecules (including DNA oligonucleotides with a Cy3 fluorescent moiety) and an aqueous salt solution with 350 mM sodium phosphate buffer and in some cases varying amounts of potassium phosphate were printed on an organic surface of a plate under 65% humidity. Volumes of 1.6 nl were printed on each spot using Scienion Sciflex printer. The plate was then put in a container, a cardboard box. Lids were put on the plate having the organic surface for transport. The plate with the spots on the organic surface was then put in a drying oven or on a hot plate (70° C.) to cause nucleation of salt crystals. After drying over a 1-hour period, the plate was irradiated to cross-link the polymer, probe biomolecules, and organic surface.

The plate was washed after printing with 10 mM NaPi Buffer to remove unbound material and then dried and stored. The plate was scanned in a Sensovation Fluorescence scanner to visually assess the spot morphology. The resulting images are shown in FIG. 11A (after washing) and FIG. 11B (after drying).

The spots in rows D and E include potassium phosphate in varying amounts (as shown in FIG. 11C), whereas the spots in the remaining rows were generated using a salt solution containing only sodium phosphate buffer. The inclusion of potassium phosphate resulted in more homogeneous and round polymer networks than spots made with sodium phosphate only (FIG. 11A-FIG. 11B). The inclusion of potassium phosphate also allows controlled crystallization when the relative humidity is not increased, for example around normal atmospheric humidity of around 40%.

7.3. Example 2: Hybridization Quality of Polymer Networks

Arrays as described in Example 1 were made using probes for detection of *S. aureus* or *E. coli*.

Primer pairs for amplifying *S. aureus* and *E. coli* were used in PCR reactions with 100 copies of *S. aureus* and *E. coli* genomic DNA, respectively, as templates, and the PCR products hybridized to arrays containing the *S. aureus* and *E. coli* probes, respectively. Results are shown in FIG. 12A-12B. FIG. 12A shows hybridization to an array of PCR product amplified from 100 copies of *S. aureus* DNA. FIG. 12B shows hybridization to an array of PCR product amplified from 100 copies of *E. coli* DNA. The probe map for the arrays of FIG. 12A and FIG. 12B is shown in FIG. 12C. This study shows that the signal from polymer networks made using an aqueous salt solution containing potassium phosphate as well as the sodium phosphate buffer have comparable signal to polymer networks made using an aqueous salt solution containing sodium phosphate only.

Surprisingly, polymer networks made using an aqueous salt solution containing potassium phosphate have a reduced background "noise" as compared to polymer networks made using an aqueous salt solution containing sodium phosphate only, as shown in FIG. 13. FIG. 13 shows quantification of fluorescence signals from hybridization of PCR product amplified using the same *S. aureus* or *E. coli*-specific primer pairs in the absence of template. Thus any hybridization signal represents background "noise". The background "noise" is absent from polymer networks made in the presence of the higher concentrations of potassium phosphate.

8. SPECIFIC EMBODIMENTS

The present disclosure is exemplified by the specific embodiments below.

1. A process for making a three-dimensional hydrogel network, comprising:
   (a) exposing a mixture (optionally positioned on the surface of a substrate), to salt crystal forming conditions comprising:
      (i) at least two types of monovalent metal ions having a total concentration of at least 500 mM,
      (ii) water-soluble polymer chains,
      (iii) cross-linker moieties, and
      (iv) optionally, probe molecules, and
      thereby forming a mixture containing one or more salt crystals;
   (b) exposing the mixture containing one or more salt crystals to cross-linking conditions, thereby forming a hydrogel containing one or more salt crystals; and
   (c) contacting the hydrogel containing one or more salt crystals with a solvent in which the one or more salt crystals are soluble, thereby dissolving the salt crystals;
   thereby forming the three-dimensional hydrogel network.
2. The process of embodiment 1, wherein the mixture comprises at least two types of monovalent metal ions having a total concentration of 500 mM to 1000 mM.
3. The process of embodiment 2, wherein total concentration of monovalent metal ions in the mixture is 550 mM to 800 mM.
4. The process of embodiment 3, wherein total concentration of monovalent metal ions in the mixture is 600 mM to 750 mM.
5. The process of any one of embodiments 1 to 4, wherein the mixture comprises two types of monovalent metal ions.
6. The process of embodiment 5, wherein the concentration of each monovalent ion is at least 150 mM or at least 200 mM.
7. The process of embodiment 5 or embodiment 6, wherein the monovalent metal ions are selected from sodium ions, potassium ions, and lithium ions.
8. The process of embodiment 5 or embodiment 6, wherein the monovalent metal ions are sodium ions and potassium ions.
9. The process of embodiment 8, wherein concentration of sodium ions is at least 300 mM.
10. The process of embodiment 9, wherein the concentration of sodium ions is 300 mM to 500 mM.
11. The process of embodiment 10, wherein the concentration of sodium ions is 300 mM to 400 mM.
12. The process of embodiment 11, wherein the concentration of sodium ions is 350 mM.
13. The process of any one of embodiments 8 to 12, wherein the concentration of potassium ions is 150 mM to 500 mM.
14. The process of embodiment 13, wherein the concentration of potassium ions is 175 mM to 400 mM.
15. The process of embodiment 14, wherein the concentration of potassium ions is 200 mM to 350 mM.
16. The process of embodiment 15, wherein the concentration of potassium ions is 250 mM to 350 mM.
17. The process of any one of embodiments 1 to 4, wherein the mixture comprises three types of monovalent metal ions.
18. The process of embodiment 17, wherein the concentration of at least two of the monovalent ions is at least 150 mM each or at least 200 mM each.
19. The process of embodiment 17 or embodiment 18, wherein the monovalent metal ions are sodium ions, potassium ions, and lithium ions.
20. The process of embodiment 19, wherein the concentration of sodium ions is at least 250 mM.
21. The process of embodiment 20, wherein the concentration of sodium ions is 250 mM to 500 mM.
22. The process of embodiment 21, wherein the concentration of sodium ions is 300 mM to 400 mM.
23. The process of embodiment 22, wherein the concentration of sodium ions is 350 mM.
24. The process of any one of embodiments 19 to 23, wherein the concentration of potassium ions is 150 mM to 500 mM.
25. The process of embodiment 24, wherein the concentration of potassium ions is 200 mM to 400 mM.
26. The process of embodiment 25, wherein the concentration of potassium ions is 250 mM to 350 mM.
27. The process of any one of embodiments 1 to 26, which further comprises, prior to step (a), forming the mixture.
28. The process of embodiment 27, wherein forming the mixture comprises combining an aqueous salt solution comprising monovalent metal cations and one or more solutions comprising the water-soluble polymer chains, the cross-linker moieties and, if present, the optional probe molecules.
29. The process of embodiment 28, wherein the water-soluble polymer chains and the cross-linker moieties are in a single solution.
30. The process of embodiment 29, wherein the cross-linked moieties are covalently attached to the polymer chains.

31. The process of any one of embodiments 28 to 30, wherein the aqueous salt solution has a pH ranging from 6 to 9.

32. The process of embodiment 31, wherein the aqueous salt solution has a pH ranging from 7 to 8.5.

33. The process of embodiment 32, wherein the aqueous salt solution has a pH of 8.

34. The process of any one of embodiments 28 to 33, wherein the aqueous salt solution comprises a solution produced by a process comprising dissolving disodium hydrogen phosphate, sodium dihydrogen phosphate, dipotassium hydrogen phosphate, potassium dihydrogen phosphate, sodium sulfate, potassium sulfate or a combination thereof in water or an aqueous solution.

35. The process of embodiment 34, wherein the aqueous salt solution is produced by a process comprising dissolving disodium hydrogen phosphate, sodium dihydrogen phosphate, dipotassium hydrogen phosphate, potassium dihydrogen phosphate, or a combination thereof in water or an aqueous solution.

36. The process of embodiment 35, wherein the aqueous salt solution is produced by a process comprising dissolving disodium hydrogen phosphate, sodium dihydrogen phosphate, dipotassium hydrogen phosphate, and potassium dihydrogen phosphate in water.

37. The process of any one of embodiments 1 to 36, wherein the concentration of phosphate ions in the mixture is at least 250 mM.

38. The process of embodiment 37, wherein the concentration of phosphate ions in the mixture is 250 mM to 1000 mM.

39. The process of embodiment 38, wherein the concentration of phosphate ions in the mixture is 550 mM to 800 mM.

40. The process of embodiment 39, wherein the concentration of phosphate ions in the mixture is 600 mM to 750 mM.

41. The process of any one of embodiments 1 to 40, wherein the salt crystal forming conditions result in formation one or more needle-shaped crystals such that one or more long channels are produced after dissolution of the salt crystals.

42. The process of any one of embodiments 1 to 41, wherein the salt crystal forming conditions result in formation of one or more compact crystals such that one or more short channels are produced after dissolution of the salt crystals.

43. The process of any one of embodiments 1 to 42, wherein the salt crystal forming conditions comprise dehydrating the mixture.

44. The process of embodiment 43, which comprises dehydrating the mixture by heating the mixture, exposing the mixture to a vacuum, reducing the humidity of the atmosphere surrounding the mixture, or a combination thereof.

45. The process of embodiment 44, which comprises dehydrating the mixture by exposing the mixture to a vacuum.

46. The process of embodiment 44, which comprises dehydrating the mixture by heating the mixture.

47. The process of embodiment 46, wherein heating the mixture comprises contacting the mixture with a gas that has a temperature which is higher than the temperature of the mixture.

48. The process of any one of embodiments 1 to 42, wherein the salt crystal forming conditions comprise cooling the mixture until the mixture becomes supersaturated with the salt.

49. The process of embodiment 48, which comprises cooling the mixture by contacting the mixture with a gas that has a temperature which is lower than the temperature of the mixture.

50. The process of any one of embodiments 1 to 49, wherein the temperature of the mixture during step (a) is maintained above the dew point of the atmosphere surrounding the mixture.

51. The process of any one of embodiments 1 to 50, wherein the cross-linker moieties activated by ultraviolet (UV) light and the cross-linking conditions comprise exposing the mixture to ultraviolet light.

52. The process of any one of embodiments 1 to 50, wherein the cross-linker moieties are activated by visible light and the cross-linking conditions comprise exposing the mixture to visible light.

53. The process of any one of embodiments 1 to 50, wherein the cross-linker moieties are activated by heat and the cross-linking conditions comprise exposing the mixture to heat.

54. The process of any one of embodiments 1 to 53, wherein the water-soluble polymer chains comprise homopolymer chains.

55. The process of any one of embodiments 1 to 54, wherein the water-soluble polymer chains comprise copolymer chains.

56. The process of any one of embodiments 1 to 54, wherein the water-soluble polymer chains comprise a mixture of homopolymer and copolymer chains.

57. The process of any one of embodiments 54 to 56, wherein the water-soluble polymer chains comprise polymer chains polymerized from one or more species of monomers.

58. The process of embodiment 57, wherein each species of monomer comprises a polymerizable group independently selected from an acrylate group, a methacrylate group, an ethacrylate group, a 2-phenyl acrylate group, an acrylamide group, a methacrylamide group, an itaconate group, and a styrene group.

59. The process of embodiment 58, wherein at least one monomer species in the water-soluble polymer comprises a methacrylate group.

60. The process of embodiment 59, wherein the at least one monomer species comprising a methacrylate group is methacryloyloxybenzophenone (MABP).

61. The process of embodiment 57, wherein the water-soluble polymer comprises a polymer polymerized from dimethylacrylamide (DMAA), methacryloyloxybenzophenone (MABP), and sodium 4-vinylbenzenesulfonate (SSNa).

62. The process of any one of embodiments 1 to 61, wherein the water-soluble polymer chains are chains of a copolymer comprising the cross-linker moieties.

63. The process of embodiment 62, wherein the water-soluble polymer chains comprise at least two cross-linker moieties per polymer molecule.

64. The process of any one of embodiments 1 to 63, wherein the cross-linker moieties are selected from benzophenone, a thioxanthone, a benzoin ether, ethyl eosin, eosin Y, rose bengal, camphorquinone, erythirosin, 4,4' azobis(4-cyanopentanoic) acid, 2,2-azobis[2-(2-imidazolin-2-yl) propane] dihydrochloride, and benzoyl peroxide.

65. The process of embodiment 64, wherein the cross-linker moieties are benzophenone moieties.

66. The process of any one of embodiments 1 to 65, wherein the solvent is water or a water-based buffer.

67. The process of embodiment 66, wherein the solvent is water.

68. The process of embodiment 66, wherein the solvent is a water-based buffer.

69. The process of embodiment 68, wherein the water-based buffer comprises phosphate, methanol, ethanol, propanol, or a mixture thereof.

70. The process of any one of embodiments 1 to 69, wherein the mixture of step (a) further comprises probe molecules.

71. The process of embodiment 70, wherein at least some, the majority or all the probe molecules comprise a nucleic acid, a nucleic acid derivative, a peptide, a polypeptide, a protein, a carbohydrate, a lipid, a cell, a ligand, or a combination thereof.

72. The process of embodiment 71, wherein at least some of the probe molecules comprise a nucleic acid or a nucleic acid derivative.

73. The process of embodiment 71, wherein at least a majority of the probe molecules comprise a nucleic acid or a nucleic acid derivative.

74. The process of embodiment 71, wherein all the probe molecules comprise a nucleic acid or a nucleic acid derivative.

75. The process of embodiment 70, wherein at least some, the majority or all the probe molecules comprise an antibody, an antibody fragment, an antigen, an epitope, an enzyme, an enzyme substrate, an enzyme inhibitor, a nucleic acid, or a combination thereof.

76. The process of embodiment 75, wherein at least some of the probe molecules comprise a nucleic acid.

77. The process of embodiment 75, wherein at least a majority of the probe molecules comprise a nucleic acid.

78. The process of embodiment 75, wherein all the probe molecules comprise a nucleic acid.

79. The process of any one of embodiments 76 to 78, wherein the nucleic acid is an oligonucleotide.

80. The process of embodiment 79, wherein the oligonucleotide is 12 to 30 nucleotides long.

81. The process of embodiment 79, wherein the oligonucleotide is 14 to 30 nucleotides long.

82. The process of embodiment 79, wherein the oligonucleotide is 14 to 25 nucleotides long.

83. The process of embodiment 79, wherein the oligonucleotide is 14 to 20 nucleotides long.

84. The process of embodiment 79, wherein the oligonucleotide is 15 to 30 nucleotides long.

85. The process of embodiment 79, wherein the oligonucleotide is 15 to 25 nucleotides long.

86. The process of embodiment 79, wherein the oligonucleotide is 15 to 20 nucleotides long.

87. The process of embodiment 79, wherein the oligonucleotide is 16 to 30 nucleotides long.

88. The process of embodiment 79, wherein the oligonucleotide is 16 to 25 nucleotides long.

89. The process of embodiment 79, wherein the oligonucleotide is 16 to 20 nucleotides long.

90. The process of embodiment 79, wherein the oligonucleotide is 15 to 40 nucleotides long.

91. The process of embodiment 79, wherein the oligonucleotide is 15 to 45 nucleotides long.

92. The process of embodiment 79, wherein the oligonucleotide is 15 to 50 nucleotides long.

93. The process of embodiment 79, wherein the oligonucleotide is 15 to 60 nucleotides long.

94. The process of embodiment 79, wherein the oligonucleotide is 20 to 55 nucleotides long.

95. The process of embodiment 79, wherein the oligonucleotide is 18 to 60 nucleotides long.

96. The process of embodiment 79, wherein the oligonucleotide is 20 to 50 nucleotides long.

97. The process of embodiment 79, wherein the oligonucleotide is 30 to 90 nucleotides long.

98. The process of embodiment 79, wherein the oligonucleotide is 20 to 100 nucleotides long.

99. The process of embodiment 79, wherein the oligonucleotide is 20 to 120 nucleotides long.

100. The process of embodiment 79, wherein the oligonucleotide is 20 to 40 nucleotides long.

101. The process of embodiment 79, wherein the oligonucleotide is 20 to 60 nucleotides long.

102. The process of embodiment 79, wherein the oligonucleotide is 40 to 80 nucleotides long.

103. The process of embodiment 79, wherein the oligonucleotide is 40 to 100 nucleotides long.

104. The process of embodiment 79, wherein the oligonucleotide is 40 to 60 nucleotides long.

105. The process of embodiment 79, wherein the oligonucleotide is 60 to 80 nucleotides long.

106. The process of embodiment 79, wherein the oligonucleotide is 80 to 100 nucleotides long.

107. The process of embodiment 79, wherein the oligonucleotide is 100 to 120 nucleotides long.

108. The process of embodiment 79, wherein the oligonucleotide is 12 to 150 nucleotides long.

109. The process of any one of embodiments 1 to 108, further comprising, prior to step (a), a step of applying the mixture to a surface of a substrate.

110. The process of embodiment 109, wherein the mixture is applied in a volume of in a volume of 100 pl to 5 nl.

111. The process of embodiment 109, wherein the mixture is applied in a volume of in a volume of 100 pl to 1 nl.

112. The process of embodiment 109, wherein the mixture is applied in a volume of in a volume of 200 pl to 1 nl.

113. The process of any one of embodiments 109 to 112, wherein the step of applying the mixture to the substrate comprises spraying the mixture onto the surface of the substrate.

114. The process of embodiment 113, wherein the mixture is sprayed by an inkjet printer.

115. The process of any one of embodiments 109 to 114, wherein the substrate comprises an organic polymer or an inorganic material having a self-assembled monolayer of organic molecules on the surface.

116. The process of embodiment 115, wherein the substrate comprises an organic polymer.

117. The process of embodiment 116, wherein the organic polymer is selected from cycloolefin copolymers, polystyrene, polyethylene, polypropylene, polycarbonate, and polymethylmethacrylate.

118. The process of embodiment 117, wherein the substrate comprises polymethylmethacrylate, polystyrene, or cycloolefin copolymers.

119. The process of embodiment 115, wherein the substrate comprises an inorganic material having an alkyl silane self-assembled monolayer on the surface.

120. The process of any one of embodiments 109 to 119, wherein the substrate comprises a microwell plate.

121. The process of any one of embodiments 109 to 120, wherein the polymer is cross-linked to the surface in step (b).

122. The process of embodiment 121, in which a water-swellable polymer is produced that is cross-linked to the surface.

123. The process of embodiment 122, wherein the water-swellable polymer can absorb up to 50 times its weight of deionized, distilled water.

124. The process of embodiment 122 or embodiment 123, wherein the water-swellable polymer can absorb 5 to 50 times its own volume of deionized, distilled water.

125. The process of any one of embodiments 122 to 124, wherein the water-swellable polymer can absorb up to 30 times its weight of saline.

126. The process of any one of embodiments 122 to 125, wherein the water-swellable polymer can absorb 4 to 30 times its own volume of saline.

127. A process for making an array, comprising generating a plurality of three-dimensional hydrogel networks by the process of any one of embodiments 1 to 126 at discrete spots on the surface of the same substrate.

128. The process of embodiment 127, wherein the three-dimensional hydrogel networks are generated simultaneously.

129. The process of embodiment 127, wherein the three-dimensional hydrogel networks are generated sequentially.

130. The process of any one of embodiments 127 to 129, further comprising cross-linking the plurality of three-dimensional hydrogel networks to the surface of the substrate.

131. A process for making an array, comprising positioning a plurality of three-dimensional hydrogel networks produced or obtainable according to the process of any one of embodiments 1 to 126 at discrete spots on a surface of the same substrate.

132. The process of any one of embodiments 127 to 131, further comprising cross-linking the plurality of three-dimensional hydrogel networks to the surface.

133. A process for making an array, comprising positioning a plurality of three-dimensional hydrogel networks produced or obtainable according to the process of any one of embodiments 109 to 126 at discrete spots on a surface of the same substrate.

134. The process of embodiment 133, wherein the positioning comprises applying the mixtures from which the three-dimensional hydrogel networks are formed at the discrete spots.

135. The process of any one of embodiments 127 to 134, wherein the spots are arranged in columns and/or rows.

136. A three-dimensional hydrogel network produced or obtainable by the process of any one of embodiments 1 to 126.

137. An array comprising a plurality of three-dimensional hydrogel networks according to embodiment 136 on a substrate.

138. An array produced or obtainable by the process of any one of embodiments 127 to 135.

139. The array of embodiment 137 or embodiment 138 which comprises at least 8 three-dimensional hydrogel networks.

140. The array of embodiment 137 or embodiment 138 which comprises at least 16 three-dimensional hydrogel networks.

141. The array of embodiment 137 or embodiment 138 which comprises at least 24 three-dimensional hydrogel networks.

142. The array of embodiment 137 or embodiment 138 which comprises at least 48 three-dimensional hydrogel networks.

143. The array of embodiment 137 or embodiment 138 which comprises at least 96 three-dimensional hydrogel networks.

144. The array of embodiment 137 or embodiment 138 which comprises at least 128 three-dimensional hydrogel networks.

145. The array of embodiment 137 or embodiment 138 which comprises at least 256 three-dimensional hydrogel networks.

146. The array of embodiment 137 or embodiment 138 which comprises at least 512 three-dimensional hydrogel networks.

147. The array of embodiment 137 or embodiment 138 which comprises at least 1024 three-dimensional hydrogel networks.

148. The array of embodiment 137 or embodiment 138 which comprises 24 to 8192 three-dimensional hydrogel networks.

149. The array of embodiment 137 or embodiment 138 which comprises 24 to 4096 three-dimensional hydrogel networks.

150. The array of embodiment 137 or embodiment 138 which comprises 24 to 2048 three-dimensional hydrogel networks.

151. The array of embodiment 137 or embodiment 138 which comprises 24 to 1024 three-dimensional hydrogel networks.

152. The array of embodiment 137 or embodiment 138 which comprises 24 three-dimensional hydrogel networks.

153. The array of embodiment 137 or embodiment 138 which comprises 48 three-dimensional hydrogel networks.

154. The array of embodiment 137 or embodiment 138 which comprises 96 three-dimensional hydrogel networks.

155. The array of embodiment 137 or embodiment 138 which comprises 128 three-dimensional hydrogel networks.

156. The array of embodiment 137 or embodiment 138 which comprises 256 three-dimensional hydrogel networks.

157. The array of embodiment 137 or embodiment 138 which comprises 512 three-dimensional hydrogel networks.

158. The array of embodiment 137 or embodiment 138 which comprises 1024 three-dimensional hydrogel networks.

159. The array of any one of embodiments 137 to 158, wherein the three-dimensional hydrogel networks comprise probe molecules, and two or more of three-dimensional hydrogel networks comprise different species of probe molecules.

160. The array of any one of embodiments 137 to 159, wherein the three-dimensional hydrogel networks comprise probe molecules, and two or more three-dimensional hydrogel networks comprise the same species of probe molecules.

161. The array of any one of embodiments 137 to 158, wherein the three-dimensional hydrogel networks comprise probe molecules, and each of the three-dimensional hydrogel networks comprise the same species of probe molecules.

162. The array of any one of embodiments 137 to 161, wherein the plurality of three-dimensional hydrogel networks comprises one or more three-dimensional hydrogel networks comprising labeled control probe molecules.

163. The array of embodiment 162, wherein the labeled control probe molecules are fluorescently labeled.

164. The array of any one of embodiments 137 to 163, wherein the substrate comprises a microwell plate and each well of the microwell plate contains no more than a single three-dimensional hydrogel network.

165. A method for determining whether an analyte is present in a sample, comprising:

(a) contacting a three-dimensional hydrogel network according to embodiment 136 or an array of any one of embodiments to 164 comprising probe molecules that are capable of binding to the analyte with the sample; and (b) detecting binding of the analyte to the probe molecules in the three-dimensional hydrogel network or array, thereby determining whether the analyte is present in the sample.

166. The method of embodiment 165, which further comprises washing the network or array comprising probe molecules between steps (a) and (b).

167. The method of embodiment 165 or embodiment 166, which further comprises contacting the network or array comprising probe molecules with a blocking reagent prior to step (a).

168. The method of any one of embodiments 165 to 167, further comprising quantifying the amount of analyte bound to the three-dimensional hydrogel network or array comprising probe molecules.

169. A method for determining whether an analyte is present in each sample in a plurality of samples, comprising:
(a) contacting an array of any one of embodiments 137 to 164 comprising probe molecules that are capable of binding to the analyte with the samples; and
(b) detecting binding of the analyte to the probe molecules in the array, thereby determining whether the analyte is present in each sample in the plurality of samples.

170. A method for determining whether an analyte is present in each sample in a plurality of samples, comprising:
(a) contacting an array of any one of embodiments 137 to 164 comprising probe molecules that are capable of binding to the analyte with the samples and comprising control probe molecules, wherein the array has been used and washed prior to step (a); and
(b) detecting binding of the analyte to the probe molecules in the array, thereby determining whether the analyte is present in each sample in the plurality of samples.

171. A method for determining whether more than one species of analyte is present in a sample, comprising:
(a) contacting an array of any one of embodiments 137 to 164 comprising different species of probe molecules that are capable of binding to the different species of analytes with the sample; and
(b) detecting binding of the analytes to the probe molecules in the array, thereby determining whether more than one species of analyte are present in the sample.

172. A method for determining whether more than one species of analyte is present in a sample, comprising:
(a) contacting an array of any one of embodiments 137 to 164 comprising different species of probe molecules that are capable of binding to the different species of analytes with the sample and comprising control probe molecules, wherein the array has been used and washed prior to step (a); and
(b) detecting binding of the analytes to the probe molecules in the array, thereby determining whether more than one species of analyte are present in the sample.

173. The method of any one of embodiments 169 to 172, in which:
(a) the substrate of the array comprises a microwell plate;
(b) each well of the microwell plate contains no more than a single three-dimensional hydrogel network; and
(c) contacting the array with the samples comprises contacting each well with no more than a single sample.

174. The method of any one of embodiments 169 to 173, which further comprises washing the array comprising probe molecules between steps (a) and (b).

175. The method of any one of embodiments 169 to 174, which further comprises contacting the array comprising probe molecules with a blocking reagent prior to step (a).

176. The method of any one of embodiments 169 to 175, further comprising quantifying the amount of analyte or analytes bound to the array.

177. The method of any one of embodiments 165 to 176, further comprising reusing the array.

178. The method of embodiment 177, wherein the array is reused at least 5 times.

179. The method of embodiment 177, wherein the array is reused at least 10 times.

180. The method of embodiment 177, wherein the array is reused at least 20 times.

181. The method of embodiment 177, wherein the array is reused at least 30 times.

182. The method of embodiment 177, wherein the array is reused at least 40 times.

183. The method of embodiment 177, wherein the array is reused at least 50 times.

184. The method of embodiment 178, which comprises reusing the array 5 to 20 times.

185. The method of embodiment 178, which comprises reusing the array 5 to 30 times.

186. The method of embodiment 178, which comprises reusing the array 10 to 50 times.

187. The method of embodiment 178, which comprises reusing the array 10 to 20 times.

188. The method of embodiment 178, which comprises reusing the array 10 to 30 times.

189. The method of embodiment 178, which comprises reusing the array 20 to 40 times.

190. The method of embodiment 178, which comprises reusing the array 40 to 50 times.

191. The method of any one of embodiments 177 to 190, which comprises washing the array between reuses.

192. The method of embodiment 191, wherein the array is washed under denaturing conditions.

193. The method of embodiment 192 wherein the denaturing conditions comprise exposing the array to heat.

194. The method of embodiment 192 wherein the denaturing conditions comprise exposing the array to low salt concentrations.

195. The method of embodiment 192 wherein the denaturing conditions comprise exposing the array to both heat and low salt concentrations.

196. The method of embodiment 192, wherein the denaturing conditions are removed prior to reuse.

197. The method of embodiment 196, wherein the denaturing conditions comprise exposing the array to heat and wherein the temperature is lowered prior to reuse.

198. The method of embodiment 196, wherein the denaturing conditions comprise exposing the array to low salt concentrations and wherein the salt concentration is increased prior to reuse.

199. The method of embodiment 196, wherein the denaturing conditions comprise exposing the array to both heat and low salt concentrations and wherein the temperature is lowered and the salt concentration is increased prior to reuse.

200. The method of any one of embodiments 177 to 199, wherein the array comprises at least one three-dimensional hydrogel network comprising a fluorescently labelled oligonucleotide as a reusability control.

201. The method of embodiment 200, which comprises testing the fluorescent signal strength.

202. The method of embodiment 201, wherein the reusability control retains at least 70% of its initial fluorescence signal strength after 10 uses.

203. The method of embodiment 202, wherein the reusability control retains at least 50% of its signal strength after 20 uses.

204. The method of any one of embodiments 200 to 203, wherein the array is no longer reused after the reusability control loses more than 50% of its signal strength.

205. The method of any one of embodiments 165 to 204, wherein analyte is a nucleic acid.

206. The method of embodiment 205, wherein the nucleic acid is a polymerase chain reaction (PCR) amplicon.

207. The method of embodiment 205, wherein the PCR amplicon is amplified from a biological sample or environmental sample.

208. The method of embodiment 207, wherein the PCR amplicon is amplified from a biological sample.

209. The method of embodiment 207, wherein the PCR amplicon is amplified from an environmental sample.

210. The method of embodiment 208, wherein the biological sample is a blood, serum, plasma, tissue, cells, saliva, sputum, urine, cerebrospinal fluid, pleural fluid, milk, tears, stool, sweat, semen, whole cells, cell constituent, cell smear, or an extract or derivative thereof.

211. The method of embodiment 210, wherein the biological sample is mammalian blood, serum or plasma or an extract thereof.

212. The method of embodiment 211, wherein the biological sample is human or bovine blood, serum or plasma or an extract thereof.

213. The method of embodiment 210, wherein the biological sample is milk or an extract thereof.

214. The method of embodiment 213, wherein the biological sample is cow's milk or an extract thereof.

215. The method of any one of embodiments 205 to 214, wherein nucleic acid is labeled.

216. The method of embodiment 215, wherein the nucleic acid is fluorescently labeled.

217. A process for making a three-dimensional hydrogel network, comprising:
  (a) exposing a mixture (optionally positioned on the surface of a substrate), to salt crystal forming conditions comprising:
    (i) at least two types of monovalent metal ions having a total concentration of at least 500 mM,
    (ii) water-soluble polymer chains,
    (iii) cross-linker moieties, and
    (iv) optionally, probe molecules, and
    thereby forming a mixture containing one or more salt crystals;
  (b) exposing the mixture containing one or more salt crystals to cross-linking conditions, thereby forming a hydrogel containing one or more salt crystals; and
  (c) contacting the hydrogel containing one or more salt crystals with a solvent in which the one or more salt crystals are soluble, thereby dissolving the salt crystals;
  thereby forming the three-dimensional hydrogel network.

218. The process of embodiment 217, wherein the mixture comprises at least two types of monovalent metal ions having a total concentration of 500 mM to 1000 mM.

219. The process of embodiment 218, wherein the mixture comprises sodium ions at a concentration of 200 mM or greater and potassium ions at a concentration of 150 mM or greater, optionally wherein:
  (a) the concentration of sodium ions ranges from 300 mM to 400 nM; and
  (b) the concentration of potassium ions ranges from 200 mM to 350 nM.

220. The process of any one of embodiments 217 to 219, which further comprises, prior to step (a), forming the mixture, optionally by combining an aqueous salt solution comprising monovalent metal cations and one or more solutions comprising the water-soluble polymer chains, the cross-linker moieties and, if present, the optional probe molecules.

221. The process of embodiment 220, wherein aqueous salt solution has a pH ranging from 6 to 9.

222. The process of embodiment 220 or embodiment 221, wherein the aqueous salt solution is produced by a process comprising dissolving disodium hydrogen phosphate, sodium dihydrogen phosphate, dipotassium hydrogen phosphate, and potassium dihydrogen phosphate in water.

223. The process of any one of embodiments 217 to 222, wherein the water-soluble polymer chains comprise methacrylate groups and at least two cross-linker moieties per molecule, optionally wherein the cross-linker moieties are benzophenone moieties.

224. The process of embodiment 223, wherein the water-soluble polymer chains are polymerized from dimethylacrylamide (DMAA), methacryloyloxybenzophenone (MABP), and sodium 4-vinylbenzenesulfonate (SSNa).

225. The process of any one of embodiments 217 to 224, wherein the mixture of step (a) comprises probe molecules, optionally wherein the probe molecules are nucleic acid molecules.

226. A three-dimensional network obtained or obtainable by the process of any one of embodiments 217 to 225.

227. An array comprising a plurality of three-dimensional networks according to embodiment 226, wherein (a) the three-dimensional networks are immobilized on the substrate and (b) each of the three-dimensional networks is located at a separate spot on the substrate, optionally wherein the array can be reused at least 10 times.

228. A process for making an array, comprising generating a plurality of three-dimensional hydrogel networks by the process of any one of embodiments 217 to 225 at discrete spots on the surface of the same substrate and cross-linking the networks to the substrate during step (b).

229. A method for determining whether an analyte is present in a sample, comprising:
  (a) contacting a three-dimensional hydrogel network according to embodiment 226 or an array of embodiment 227, said network or array comprising probe molecules that are capable of binding to the analyte with the sample; and
  (b) detecting binding of the analyte to the probe molecules in the three-dimensional hydrogel network or array, thereby determining whether the analyte is present in the sample.

230. The method of embodiment 229, wherein the network or array has been used and washed at least 10 times prior to step (a) or which further comprises reusing the network or array at least 10 times following step (b).

231. The method of embodiment 230, which further comprises quantifying binding of the analyte to the probe molecules in the three-dimensional network.

While various specific embodiments have been illustrated and described, it will be appreciated that various changes can be made without departing from the spirit and scope of the disclosure(s).

9. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. An array comprising a plurality of three-dimensional hydrogel networks immobilized on a substrate, wherein the three-dimensional hydrogel networks:
   (a) comprise crosslinked water-soluble polymer chains and one or more probe molecules; and
   (b) have one or more long transport channels and one or more short transport channels.

2. The array of claim 1, wherein the water-soluble polymer chains comprise polymer chains polymerized from dimethylacrylamide (DMAA), methacryloyloxybenzophenone (MABP), and sodium 4-vinylbenzenesulfonate (SSNa).

3. The array of claim 1, wherein the probe molecules are nucleic acid molecules.

4. The array of claim 2, wherein the probe molecules are nucleic acid molecules.

5. The array of claim 1, wherein the probe molecules are crosslinked to the crosslinked water-soluble polymer chains.

6. The array of claim 2, wherein the probe molecules are crosslinked to the crosslinked water-soluble polymer chains.

7. The array of claim 3, wherein the probe molecules are crosslinked to the crosslinked water-soluble polymer chains.

8. The array of claim 4, wherein the probe molecules are crosslinked to the crosslinked water-soluble polymer chains.

9. The array of claim 1, wherein the plurality of three-dimensional hydrogel networks comprises one or more three-dimensional hydrogel networks comprising labeled control probe molecules.

10. The array of claim 9, wherein the labeled control probe molecules are fluorescently labeled.

11. The array of claim 1, wherein the three-dimensional hydrogel networks are crosslinked to the substrate.

12. The array of claim 1, wherein the three-dimensional hydrogel networks are positioned at discrete spots on the substrate.

13. The array of claim 1, wherein the one or more short transport channels are formed from cubic or rod-shaped salt crystals.

14. The array of claim 1, wherein at least one of the three-dimensional networks comprises one or more short transport channels penetrated by one or more long transport channels.

15. The array of claim 1, wherein the one or more long transport channels are formed from needle-shaped salt crystals.

16. The array of claim 13, wherein the one or more long transport channels are formed from needle-shaped salt crystals.

17. A method for determining whether an analyte is present in a sample, comprising:
   (a) contacting the array of claim 1 with the sample, wherein the array comprises one or more three-dimensional hydrogel networks comprising probe molecules that are capable of binding to the analyte; and
   (b) detecting binding of the analyte to the probe molecules.

18. The method of claim 17, wherein the network has been used and washed at least 10 times prior to step (a).

19. The method of claim 17, which further comprises reusing the network at least 10 times following step (b).

20. The method of claim 17, which further comprises quantifying binding of the analyte to the probe molecules.

21. The method of claim 17, wherein the array comprises at least one three-dimensional hydrogel network comprising a fluorescently labelled oligonucleotide as a reusability control.

22. The method of claim 21, which comprises testing the fluorescent signal strength.

23. The method of claim 22, wherein the reusability control retains at least 70% of its initial fluorescence signal strength after 10 uses.

* * * * *